United States Patent [19]
Dietliker et al.

[11] Patent Number: 6,017,675
[45] Date of Patent: Jan. 25, 2000

[54] OXIMESULFONIC ACID ESTERS AND THE USE THEREOF AS LATENT SULFONIC ACIDS

[75] Inventors: Kurt Dietliker, Fribourg, Switzerland; Martin Kunz, Efringen-Kirchen, Germany

[73] Assignee: Ciba Specialty Chemicals Corporation, Tarrytown, N.Y.

[21] Appl. No.: 08/738,560

[22] Filed: Oct. 28, 1996

[30] Foreign Application Priority Data

Oct. 31, 1995 [CH] Switzerland .................. 3080/95

[51] Int. Cl.⁷ .................................. G03C 1/492
[52] U.S. Cl. ............... 430/270.1; 430/919; 430/921; 522/59
[58] Field of Search .................. 430/270.1, 921; 522/59

[56] References Cited

U.S. PATENT DOCUMENTS

| | | | |
|---|---|---|---|
| 4,347,372 | 8/1982 | Föry et al. | 548/217 |
| 4,451,286 | 5/1984 | Martin | 71/107 |
| 4,540,598 | 9/1985 | Berner et al. | 427/54.1 |
| 4,715,883 | 12/1987 | Lukaszczyk et al. | 71/90 |
| 4,736,055 | 4/1988 | Dietliker et al. | 560/13 |
| 5,714,625 | 2/1998 | Hada et al. | 558/437 |

FOREIGN PATENT DOCUMENTS

| | | |
|---|---|---|
| 0012158 | 6/1980 | European Pat. Off. . |
| 0048615 | 3/1982 | European Pat. Off. . |
| 0139609 | 5/1985 | European Pat. Off. . |
| 0199672 | 10/1986 | European Pat. Off. . |
| 0241423 | 10/1987 | European Pat. Off. . |
| 0361907 | 4/1990 | European Pat. Off. . |
| 0571330 | 11/1993 | European Pat. Off. . |
| 0592139 | 4/1994 | European Pat. Off. . |
| 2084573 | 4/1982 | United Kingdom . |

OTHER PUBLICATIONS

Abstract Derwent No. B7–286243/41 of EP–241423.
Derwent Abstract 93–370703/47 of EP 571,330.

*Primary Examiner*—Janet Baxter
*Assistant Examiner*—Rosemary Ashton
*Attorney, Agent, or Firm*—Luther A. R. Hall; David R. Crichton

[57] ABSTRACT

The invention relates to the use of oximesulfonic acid esters of formula I

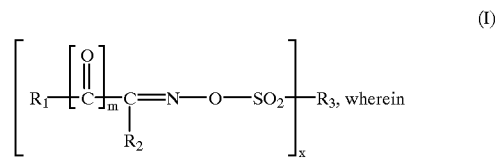

m is 0 or 1 and x is 1 or 2; $R_1$ is, for example, substituted phenyl, $R_2$ has, for example, one of the meanings of $R_1$ or is unsubstituted phenyl, $C_1$–$C_6$alkanoyl, unsubstituted or substituted benzoyl, $C_2$–$C_6$alkoxycarbonyl or phenoxycarbonyl; or $R_1$ and $R_2$, if necessary together with the CO group, form a ring, $R_3$, when x is 1, is, for example, $C_1$–$C_{18}$alkyl, phenyl or phenanthryl, the radicals phenyl and phenanthryl being unsubstituted or substituted, or $R_3$, when x is 2, is, for example, $C_2$–$C_{12}$alkylene, phenylene or oxydiphenylene, the radicals phenylene and oxydiphenylene being unsubstituted or substituted, as latent acid donors, especially at wavelengths over 390 nm, and to the use of the compounds in the production of photoresists.

14 Claims, No Drawings

OXIMESULFONIC ACID ESTERS AND THE USE THEREOF AS LATENT SULFONIC ACIDS

The invention relates to photopolymerisable compositions comprising oximesulfonic acid esters, and to the use of the compounds as long-wavelength-activatable latent sulfonic acid photoinitiators.

EP-A-139 609 discloses surface-coating compositions based on photosensitive oxime sulfonates and customary acid-curable resins.

EP-A-571 330 discloses the use of α-(4-toluene-sulfonyloxyimino)-4-methoxybenzyl cyanide and α-(4-toluene-sulfonyloxyimino)-3-thienylmethyl cyanide as latent acid donors in positive and negative photoresists for wavelengths of 340–390 nm, especially those in the radiation region of the mercury i line (365 nm).

In the art, a need still exists, especially in the case of irradiation with long wavelength light, for reactive non-ionic latent acid donors that are thermally and chemically stable and that, after being activated by light, can be used as catalysts for a variety of acid-catalysed reactions, such as polycondensation reactions, acid-catalysed depolymerisation reactions, acid-catalysed electrophilic substitution reactions or the acid-catalysed removal of protecting groups. There is also a need for compounds that when irradiated with light are converted into acids and are capable of acting as solubility inhibitors in resist formulations.

Surprisingly, it has now been found that specific oximesulfonates are especially suitable as catalysts for such reactions.

The invention accordingly relates to a photoactivatable composition comprising a) at least one compound that can be crosslinked under the action of an acid and/or b) at least one compound the solubility of which is altered under the action of an acid and c) as photoinitiator, at least one compound of formula I

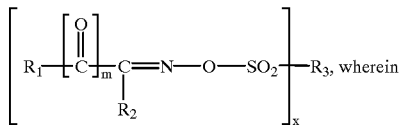

m is 0 or 1 and x is 1 or 2;

$R_1$ is phenyl substituted by one or more of the radicals $C_1$–$C_{12}$alkyl, $C_1$–$C_4$haloalkyl, phenyl, $OR_4$, $SR_4$ and/or $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the phenyl ring, with the proviso that when the phenyl ring is substituted by methoxy at least one further substituent must be present on the ring, or $R_1$ is naphthyl, anthracyl or phenanthryl, the radicals naphthyl, anthracyl and phenanthryl being unsubstituted or substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the naphthyl, anthracyl or phenanthryl ring, or $R_1$ is a heteroaryl radical that is unsubstituted or substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the heteroaryl ring, with the proviso that $R_1$ is not unsubstituted thienyl;

$R_2$ has one of the meanings of $R_1$ or is unsubstituted or CN-substituted phenyl, $C_2$–$C_6$-alkanoyl, benzoyl that is unsubstituted or substituted by $C_1$–$C_6$alkyl, phenyl, $OR_4$, $SR_4$ and/or by $NR_5R_6$, $C_2$–$C_6$alkoxycarbonyl, phenoxycarbonyl, $R_5R_6N$, morpholino, piperidino, CN, $C_1$–$C_4$haloalkyl, $S(O)_nC_1$–$C_6$alkyl, unsubstituted or $C_1$–$C_{12}$alkyl-substituted $S(O)$n-$C_6$–$C_{12}$aryl, $SO_2O$—$C_1$–$C_6$alkyl, $SO_2O$—$C_6$–$C_{10}$aryl or $NHCONH_2$, wherein n is 1 or 2; or $R_1$ and $R_2$, if appropriate together with the CO group, form a 5- or 6-membered ring that is unsubstituted or substituted by $C_1$–$C_6$alkyl, phenyl, $OR_4$, $SR_4$ or by $NR_5R_6$ and that may additionally be interrupted by O, S, $NR_5$ and/or by CO and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or substituted by one or more of the radicals halogen, $C_1$–$C_4$haloalkyl, CN, $NO_2$, $C_1$–$C_{16}$alkyl, phenyl, $OR_4$, $COOR_7$, —OCO—$C_1$–$C_4$alkyl, $SO_2OR_7$ and/or by $R_5R_6N$, or $R_3$, when x is 2, is $C_2$–$C_{12}$alkylene, phenylene, naphthylene,

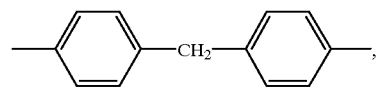

diphenylene or oxydiphenylene, the radicals phenylene, naphthylene,

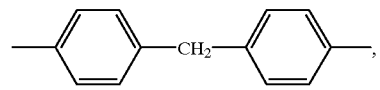

diphenylene and oxydiphenylene being unsubstituted or substituted by $C_1$–$C_{12}$alkyl;

$R_4$ is hydrogen, $C_1$–$C_{12}$alkyl that is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—, or is phenyl;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring which may be interrupted by —O— or by —$NR_4$—; and $R_7$ is $C_1$–$C_{12}$alkyl that is unsubstituted or substituted by OH and/or by $C_1$–$C_4$alkoxy and that may additionally be interrupted by —O—.

$C_1$–$C_{18}$Alkyl is linear or branched and is, for example, $C_1$–$C_{12}$-, $C_1$–$C_8$-, $C_1$–$C_6$- or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl. For example, $R_3$ is $C_1$–$C_8$alkyl, especially $C_1$–$C_6$alkyl, preferably $C_1$–$C_4$alkyl, such as methyl, isopropyl or butyl.

$C_1$–$C_{16}$Alkyl and $C_1$–$C_{12}$alkyl are likewise linear or branched and are, for example, as defined above up to the appropriate number of carbon atoms. Of interest are, for example, $C_1$–$C_8$-, especially $C_1$–$C_6$-, preferably $C_1$–$C_4$-alkyl, such as methyl or butyl. $C_2$–$C_{12}$Alkyl, which is interrupted once or several times by —O— or by —S—, is interrupted, for example, from one to five times, for example from one to three times or once or twice, by —O—. That results in structural units such as: —S($CH_2$)$_2$OH, —O($CH_2$)$_2$OH, —O($CH_2$)$_2$O$CH_3$, —O($CH_2CH_2$O)$_2$$CH_2CH_3$, —$CH_2$—O—$CH_3$, —$CH_2CH_2$—O—$CH_2CH_3$, —[$CH_2CH_2$O]$_y$—$CH_3$, wherein y=1–5, —($CH_2CH_2$O)$_5$$CH_2CH_3$, —$CH_2$—CH($CH_3$)—O—$CH_2$—$CH_2CH_3$ or —CH($CH_3$)—O—$CH_2$—$CH_3$.

$C_5$–$C_{12}$Cycloalkyl is, for example, cyclopentyl, cyclohexyl, cyclooctyl, cyclododecyl, especially cyclopentyl and cyclohexyl, preferably cyclohexyl.

$C_2$–$C_{12}$Alkylene is linear or branched and is, for example, $C_2$–$C_8$-, $C_2$–$C_6$- or $C_2$–$C_4$-alkyl Examples are ethylene, propylene, butylene, pentylene, hexylene, heptylene, octylene, nonylene, decylene, undecylene and dodecylene. For example, $R_3$ is $C_1$–$C_8$alkylene, especially $C_1$–$C_6$alkylene, preferably $C_1$–$C_4$alkylene, such as methylene or butylene.

Substituted phenyl carries from one to five, for example one, two or three, especially one or two, substituents on the phenyl ring. The substitution is preferably in the 4-, 3,4-, 3,5- or 3,4,5-position of the phenyl ring.

When the radicals naphthyl, phenanthryl, heteroaryl and anthracyl are substituted by one or more radicals, they are, for example, mono- to penta-substituted, for example mono-, di- or tri-substituted, especially mono- or di-substituted.

When $R_1$ is a substituted phenyl radical substituted by $OR_4$, $SR_4$ and/or by $NR_5R_6$ and the substituents $OR_4$, $SR_4$ and $NR_5R_6$ form 5- or 6-membered rings, via the radicals $R_4$, $R_5$ or $R_6$, with other substituents or with one of the carbon atoms of the phenyl ring, for example the following structural units are obtained

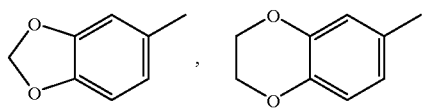

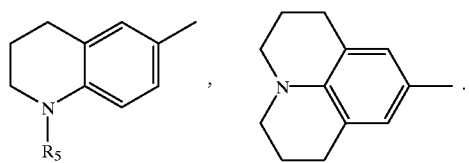

In the present Application, the term "heteroaryl" denotes unsubstituted and substituted radicals, for example 2-thienyl,

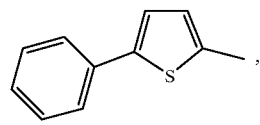

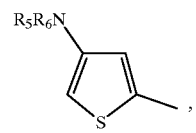

wherein $R_5$ and $R_6$ are as defined above, thianthrenyl, isobenzofuranyl, xanthenyl, phenoxathiin,

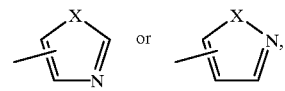

wherein X is S, O or $NR_5$ and $R_5$ is as defined above. Examples thereof are pyrazolyl, thiazolyl, oxazolyl, isothiazolyl or isoxazolyl.

Also included are, for example, furyl, pyrrolyl, 1,2,4-triazolyl,

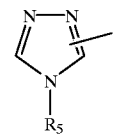

or 5-membered ring heterocycles having a fused-on aromatic compound, for example benzimidazolyl, benzothienyl, benzofuranyl, benzoxazolyl and benzothiazolyl.

Other examples of "heteroaryls" are pyridyl, especially 3-pyridyl,

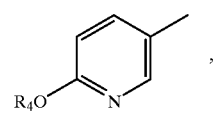

wherein $R_4$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

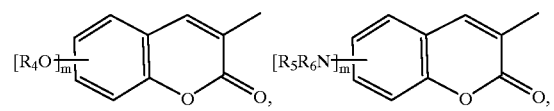

wherein $R_4$, $R_5$, $R_6$ and m are as defined above,

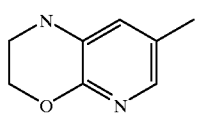

or anthraquinonyl. Each of the heteroaryls may carry the substituents indicated above or in claim 1.

Camphoryl is

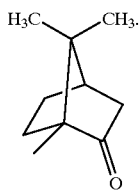

When $R_1$ and $R_2$, if appropriate together with the CO group, form a 5- or 6-membered ring, it is, for example, a cyclopentane, cyclohexane, pyran or piperidine ring. There may be fused to that ring, for example, also benzo, naphtho, anthraceno, phenanthreno or heteroaryl radicals, there being formed structures such as

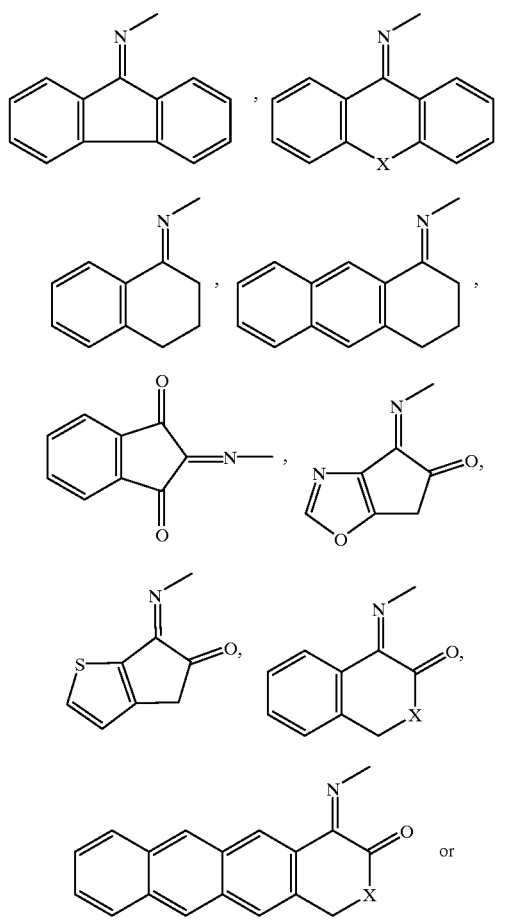

wherein X is S, O or $NR_5$ and $R_5$ is as defined above, in which structures the aromatic rings may carry further substituents as defined above or in claim 1. They are, for example, also tetrahydronaphthalene, dihydroanthracene, indan, chroman, fluorene, xanthene or thioxanthene ring systems. When the ring contains carbonyl groups, for,example benzoquinone, naphthoquinone or anthraquinone radicals are formed.

$C_1$–$C_6$Alkanoyl is, for example, formyl, acetyl, propionyl, butanoyl or hexanoyl, especially acetyl.

$C_1$–$C_4$Alkoxy is, for example, methoxy, ethoxy, propoxy and butoxy, it being possible for the alkyl radicals in alkoxy groups having more than two carbon atoms also to be branched.

$C_2$–$C_6$Alkoxycarbonyl is ($C_1$–$C_5$alkyl)—O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyl, it being possible for the alkyl radicals in alkoxy groups having more than two carbon atoms also to be branched.

$C_1$–$C_{10}$Haloalkyl and $C_1$–$C_4$haloalkyl are $C_1$–$C_{10}$- and $C_1$–$C_4$-alkyl mono- or poly-substituted by halogen, $C_1$–$C_{10}$- and $C_1$–$C_4$-alkyl being, for example, as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl.

Halogen is fluorine, chlorine, bromine or iodine, especially chlorine or fluorine, preferably fluorine.

In a group $S(O)_n$—$C_6$–$C_{10}$aryl that may be unsubstituted or substituted by $C_1$–$C_{12}$alkyl, the aryl radical is phenyl, tosyl, dodecylsulfonyl or 1- or 2-naphthyl.

Phenyl-$C_1$–$C_3$alkyl is, for example, benzyl, 2-phenylethyl, 3-phenylpropyl, α-methylbenzyl or α,α-dimethylbenzyl, especially benzyl.

Oxydiphenylene is

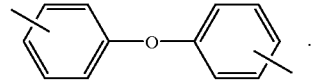

When $R_5$ and $R_6$ together with the nitrogen atom to which they are bonded form a 5-, 6- or 7-membered ring that may be interrupted by —O— or by —$NR_4$—, for example the following structures are obtained

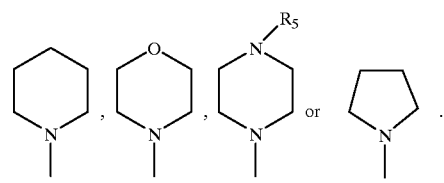

Preference is given to compositions wherein in compounds of formula I $R_1$ is phenyl substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the phenyl ring.

Further compositions of interest are those wherein in the compounds of formula I $R_1$ is a heteroaryl radical that is unsubstituted or mono- or poly-substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the heteroaryl ring.

Special mention should be made of compositions wherein in the compounds of formula I $R_2$ is $C_2$–$C_6$alkoxycarbonyl, CN, $C_1$–$C_4$haloalkyl, $S(O)_nC_1$–$C_6$alkyl, or unsubstituted or $C_1$–$C_{12}$alkyl-substituted $S(O)_n$—$C_6$–$C_{10}$aryl.

Preference is given especially to compositions I wherein in the compounds of formula I $R_4$ is $C_1$–$C_6$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—.

Compositions of interest are those wherein in the compounds of formula I m is 0 and x is 1.

Preference is given also to compositions wherein in the compounds of formula I $R_3$ is $C_1$–$C_{18}$alkyl, $C_1$–$C_{10}$haloalkyl, or phenyl that is unsubstituted or substituted by halogen, $NO_2$, $C_1$–$C_4$haloalkyl, $C_1$–$C_{12}$alkyl, $OR_4$, $COOR_7$ and/or by —OCO—$C_1$–$C_4$alkyl.

Preference is given likewise to compositions wherein in the compounds of formula I m is 0 and x is 1, $R_1$ is 3,4-dimethoxyphenyl, 3,4-di(methylthio)phenyl, 3-methoxy-4-methylthiophenyl $R_2$ is CN or 4-cyanophenyl, and $R_3$ is phenyl, 4-methylphenyl, 4-methoxyphenyl, 3-trifluoromethylphenyl, 4-chlorophenyl, methyl, isopropyl, n-octyl, 2,4,6-(triisopropyl)-phenyl, 4-nitrophenyl, 2,4,6-trimethylphenyl or dodecylphenyl or $R_1$ and $R_2$ together form a fluorene system in which the aromatic rings are substituted by methoxy or hydroxyethylthio groups.

The invention relates also to the use of compounds of formula I according to claim 1 as photoinitiators for compounds that can be crosslinked under the action of an acid and/or as solubility inhibitors for compounds the solubility of which is altered under the action of an acid.

In photocrosslinkable compositions, oximesulfonic acid esters act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Finally, oximesulfonic acid esters that are sparingly soluble in an aqueous-alkaline developer can be rendered soluble in the developer by means of light-induced conversion into the free acid, with the result that they can be used as solubility inhibitors in combination with suitable film-forming resins.

Resins that can be crosslinked by acid catalysis are, for example, mixtures of polyfunctional alcohol s or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

In addition, oximesulfonates can be used, for example, as light-activatable hardeners for siloxane group-containing resins. Those resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. That type of polycondensation of polysiloxanes is described, for example, in J. J. Lebrun, H. Pode, Comprehensive Polymer Science, Volume 5, page 593, Pergamon Press, Oxford, 1989.

It is desirable in those reactions for the acid to be released also when irradiated with long wavelength light. Surprisingly, it has been found that some oximesulfonic acid esters are capable of releasing the acid even when irradiated with long wavelength light of more than 390 nm.

The invention therefore relates also to the use of compounds of formula Ia

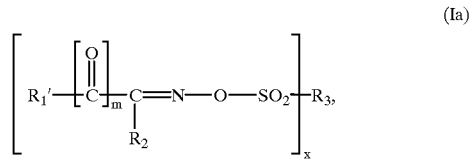

(Ia)

wherein m is 0 or 1 and x is 1 or 2;

$R_1'$ is phenyl mono- or poly-substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the phenyl ring, or $R_1'$ is naphthyl, anthracyl or phenanthryl, the radicals naphthyl, anthracyl and phenanthryl being unsubstituted or mono- or poly-substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$ or $R_5$, with further substituents or with one of the carbon atoms of the naphthyl, anthracyl or phenanthryl ring, or $R_1'$ is a heteroaryl radical that is unsubstituted or substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5-or 6-membered rings, via the radicals $R_4$, $R_5$ and/or $R_6$, with further substituents or with one of the carbon atoms of the heteroaryl ring;

$R_2$ has one of the meanings of $R_1'$ or is unsubstituted phenyl, $C_1$–$C_6$alkanoyl, benzoyl that is unsubstituted or substituted by $C_1$–$C_6$alkyl, phenyl, $OR_4$, $SR_4$ and/or by $NR_5R_6$, $C_2$–$C_6$alkoxy-carbonyl, phenoxycarbonyl, $R_5R_6N$, morpholino, piperidino, CN, $C_1$–$C_4$haloalkyl, $S(O)_nC_1$–$C_6$-alkyl, unsubstituted or $C_1$–$C_{12}$alkyl-substituted $S(O)n$—$C_6$–$C_{12}$aryl, $S(O)_2O$—$C_1$–$C_6$alkyl, $SO_2O$—$C_6$–$C_{10}$aryl or $NHCONH_2$, wherein n is 1 or 2; or $R_1'$ and $R_2$, if appropriate together with the CO group, form a 5- or 6-membered ring that is unsubstituted or substituted by $C_1$–$C_6$alkyl, phenyl, $OR_4$, $SR_4$ or by $NR_5R_6$ and that may additionally be interrupted by O, S, CO and/or by $NR_5$ and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or mono- or poly-substituted by halogen, $C_1$–$C_4$haloalkyl, CN, $NO_2$, $C_1$–$C_{16}$alkyl, $OR_4$, $COOR_7$, —OCO—$C_1$–$C_4$alkyl, $SO_2OR_7$ and/or by $R_5R_6N$, or $R_3$, when x is 2, is $C_2$–$C_{12}$alkylene, phenylene, naphthylene,

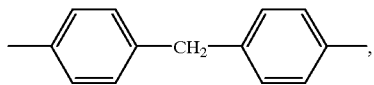

diphenylene or oxydiphenylene, the radicals phenylene, naphthylene,

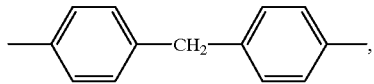

diphenylene and oxydiphenylene being unsubstituted or substituted by $C_1$–$C_{12}$alkyl; $R_4$ is hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl and that may additionally be interrupted by —O—;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_1$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring that may be interrupted by —O— or by —$NR^4$—; and $R_7$ is $C_1$–$C_{12}$alkyl that is unsubstituted or substituted by OH and/or by $C_1$–$C_4$alkoxy and that may additionally be interrupted by —O—, as photosensitive acid donors for radiation at wavelengths over 390 nm.

That use is of interest especially for compounds of formula Ia wherein $R_1'$ is phenyl substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the phenyl ring.

That use is furthermore of interest for compounds of formula Ia wherein $R_1'$ is a heteroaryl radical that is unsubstituted or substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$ or $R_5$, with further substituents or with one of the carbon atoms of the heteroaryl ring. The invention relates also to the novel oximesulfonic acid esters of formula Ib

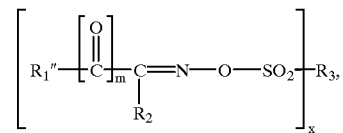

(Ib)

wherein m is 0 or 1 and x is 1 or 2;

$R_1''$ is phenyl mono- or poly-substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the phenyl ring, or $R_1''$ is naphthyl, anthracyl or phenanthryl, the radicals naphthyl, anthracyl and phenanthryl being unsubstituted or mono- or poly-substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the naphthyl, anthracyl or phenanthryl ring, or $R_1''$ is a heteroaryl radical that is unsubstituted or substituted by $C_1$–$C_6$alkyl, phenyl, $OR_4$, $SR_4$ and/or by $NR_5R_6$, it being possible for the substituents $OR_4$, $SR_4$ and $NR_5R_6$ to form 5- or 6-membered rings, via the radicals $R_4$, $R_5$ and/or $R_6$, with further substituents or with one of the carbon atoms of the heteroaryl ring, with the proviso that $R_1''$ is not unsubstituted thienyl;

$R_2$ has one of the meanings of $R_1''$ or is unsubstituted phenyl, $C_1$–$C_6$alkanoyl, benzoyl that is unsubstituted or substituted by $C_1$–$C_6$alkyl, phenyl, $OR_4$, $SR_4$ and/or by $NR_5R_6$, $C_2$–$C_6$alkoxy-carbonyl, phenoxycarbonyl, $R_5R_6N$, morpholino, piperidino, CN, $C_1$–$C_4$haloalkyl, $S(O)_nC_1$–$C_6$-alkyl, unsubstituted or $C_1$–$C_{12}$alkyl-substituted $S(O)n$-$C_6$–$C_{10}$aryl, $SO_2O$-$C_1$–$C_6$alkyl, $SO_2O$-$C_6$–$C_{10}$aryl or $NHCONH_2$, wherein n is 1 or 2, or $R_1''$ and $R_2$, if appropriate together with the CO group, form a 5- or 6-membered ring that is unsubstituted or substituted by $C_1$–$C_6$alkyl, phenyl, $OR_4$, $SR_4$ or by $NR_5R_6$ and that may additionally be interrupted by O, S, $NR_5$ and/or by CO and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or mono- or poly-substituted by halogen, $C_1$–$C_4$haloalkyl, CN, $NO_2$, $C_1$–$C_{16}$alkyl, $OR_4$, $COOR_7$, —OCO—$C_1$–$C_4$alkyl, $SO_2OR_7$ and/or by $R_5R_6N$, with the proviso that when $R_3$ is phenyl, 3-chlorophenyl or 4-methylphenyl, R, as a methoxy-substituted phenyl ring must contain at least one further substituent on the ring, which substituent is not, however, methoxy or methyl, and with the proviso that no two of the substituents $OR_4$ form a 1,3-dioxolan ring, or $R_3$, when x is 2, is $C_2$–$C_{12}$alkylene, phenylene, naphthylene,

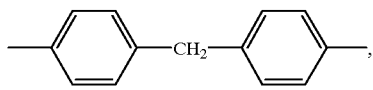

diphenylene or oxydiphenylene, the radicals phenylene, naphthylene,

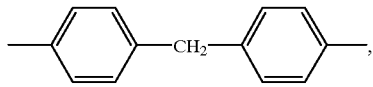

diphenylene and oxydiphenylene being unsubstituted or substituted by $C_1$–$C_{12}$alkyl;

$R_4$ is hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl and that may additionally be interrupted by —O—;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_1$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring that may be interrupted by —O— or by —$NR_4$—; and $R_7$ is $C_1$–$C_{12}$alkyl that is unsubstituted or substituted by OH and/or by $C_1$–$C_4$alkoxy and that may additionally be interrupted by —O—.

Of special interest are the compounds α-(methylsulfonyloxyimino)-3,4-dimethoxy-benzyl cyanide, α-(4-dodecylphenylsulfonyloxyimino)-3,4-dimethoxybenzyl cyanide or α-(4-methyl-phenylsulfonyloxyimino)-4-thiomethylbenzyl cyanide, α-(2-propylsulfonyloxyimino)- 3,4-dimethoxybenzyl cyanide, α-(phenylsulfonyloxyimino)-3,4-dimethoxybenzyl cyanide, α-(4-methoxyphenylsulfonyloxyimino)-3,4-dimethoxybenzyl cyanide, α-(2,4,6-tris(isopropyl)-phenylsulfonyloxyimino)-3,4-dimethoxybenzyl cyanide, α-(n-octylsulfonyloxyimino)-3,4-dimethoxybenzyl cyanide, α-(4-chlorophenylsulfonyloxyimino)-3,4-dimethoxybenzyl cyanide, α-(3-trifluoromethylphenylsulfonyloxyimino)-3,4-dimethoxybenzyl cyanide, α-(methyl-sulfonyloxyimino)-4-methylthiobenzyl cyanide, α-(4-dodecylphenylsulfonyloxyimino)-4-methylthiobenzyl cyanide, 9-(4-methylphenylsulfonyloxyimino)-3,6-dimethoxyfluorene, 9-(4-dodecylphenylsulfonyloxyimino)-3,6-dimethoxyfluorene, 9-(4-methylphenylsulfonyloxyimino)-1,6-dimethoxyfluorene, 9-(4-dodecylphenylsulfonyloxyimino)-1,6-dimethoxyfluorene, α-(2,4,6-tris(methyl) phenylsulfonyloxyimino)-3,4-dimethoxybenzyl cyanide, α-(4-nitrophenylsulfonyloxyimino)-3,4-dimethoxybenzyl cyanide, α-(2-propylsulfonyloxyimino)-4-methylthiobenzyl cyanide, α-(4-chlorphenylsulfonyloxyimino)-4-methylthiobenzyl cyanide, α-(3-trifluormethylphenylsulfonyloxy-imino)-4-methylthiobenzyl cyanide, α-(4-nitrophenylsulfonyl-oxyimino)-4-methylthiobenzyl cyanide, α-(methylsulfonyloxyimino)-3,4-dithiomethylbenzyl cyanide, α-(4-methylphenylsulfonyloxy-imino)-3,4-dithiomethylbenzyl cyanide, α-(4-methylphenylsulfonyl-oxyimino)-3-methoxy-4-methylthio-benzyl cyanide, α-(methylsulfonyloxyimino)-3-methoxy-4-methylthio-benzyl cyanide, 9-(n-octylsulfonyloxyimino)-3,6-dimethoxy-fluorene, 9-(4-dodecylphenylsulfonyloxyimino)-3,6-di(4-hydroxyethylthio)-fluorene, 3-(para-cyano-1-[4-dodecylphenylsulfonyloxyimino]-benzyl)-5,7-dibutoxy-coumarine.

The invention relates also to mixtures of isomeric forms of the compounds of formula I, Ia or Ib.

Oximesulfonic acid esters (of formulae I, Ia and Ib) can be prepared by methods described in the literature, for example by reacting suitable free oximes (of formula II) with sulfonic acid halides (of formula III) in the presence of a base, such as triethylamine, or by reaction of the salt of an oxime with a sulfonic acid chloride. Those methods are disclosed, for example, in EP-A 48615.

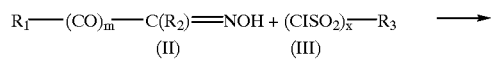

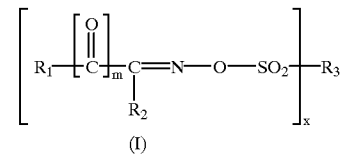

The reaction is advantageously carried out in an inert organic solvent in the presence of a tertiary amine.

The sodium salts of oximes can be obtained, for example, by reacting the oxime in question with a sodium alcoholate in DMF.

Oximesulfonic acid derivatives having a heterocyclic aromatic 5-membered ring substituent can also be prepared by 1,3-dipolar cycloaddition of suitable sulfonic acid derivatives, for example the esters of oximinomalodinitrile or oximinocyanoacetic acid ester, to a suitable 1,3-dipolar compound, such as a nitrile oxide. A synthesis of that type is described, for example, in J. Perrocheau, R. Carré, Bull. Soc. Chim. Belge 1994, 103, 9.

Oximesulfonic acid esters can be present both in the syn (cis) and the anti (trans) form or as mixtures of the two conformational isomers. In the present invention, both the individual conformational isomers and any mixtures of the two conformational isomers can be used.

The oximes of formula II required for reaction can be prepared analogously to known processes, for example by reacting compounds having reactive methylene groups, such as benzyl cyanide derivatives or phenylacetic acid derivatives, with an alkyl nitrite, for example methyl nitrite or isoamyl nitrite, and a sodium alcoholate, for example sodium methanolate. Such reactions are described, for example, in "The systematic identification of organic compounds", John Wiley and Sons, New York, 1980, p. 181, "Die Makromolekulare Chemie" (Macromolecular Chemistry), 1967, 108, 170, or "Organic Synthesis", 1979, 59, 95. Oximes can also be obtained by reacting a corresponding carbonyl compound or thionylcarbonyl compound with hydroxylamine.

A further possibility is the nitrosation of hydroxy-aromatic compounds.

The preparation of sulfonic acid halides (of formula III) is familiar to a person skilled in the art and is described, for example, in customary chemistry textbooks.

Oximesulfonic acid esters can be used as light-activatable hardeners for acid-curable resins. Suitable acid-curable resins are all resins the curing of which can be accelerated by acid catalysts, such as aminoplasts or phenolic resole resins. Those resins are especially melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4th Edition, Volume 15 (1978), pages 613 to 628, or Ullmann's Encyclopedia of Industrial Chemistry, Verlag Chemie, 1991, Vol. 18, 360 ff., Vol. A19, 371 ff.

The surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. As already mentioned above, for example polysiloxanes can also be crosslinked using acid catalysis. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I, Ia or Ib. In that process, a) radical polymerisation initiators or b) photoinitiators can additionally be used. The former initiate polymerisation of the unsaturated groups during heat treatment, the latter during UV irradiation.

Examples of additional photoinitiators are, for example, radical photoinitiators, such as those from the class of the benzophenones, acetophenone derivatives, such as α-hydroxycycloalkylphenyl ketone, dialkoxyacetophenone, α-hydroxy- or α-amino-acetophenone, 4-aroyl-1,3-dioxolans, benzoin alkyl ethers and benzil ketals, monoacylphosphine oxides, bisacylphosphine oxides or titanocenes. Examples of especially suitable additional photoinitiators are: 1-(4-dodecylbenzoyl)-1-hydroxy-1-methyl-ethane, 1-(4-isopropylzoyl)-1-hydroxy-1-methyl-ethane, 1-benzoyl-1-hydroxy-1-methyl-ethane, 1-[4-(2-hydroxyethoxy)-benzoyl]-1-hydroxy-1-methyl-ethane, 1-[4-(acryloyloxyethoxy)-benzoyl]-1-hydroxy-1-methyl-ethane, diphenyl ketone, phenyl-1-hydroxy-cyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzoyl)-1-methyl-1-morpholino-ethane, benzil dimethyl ketal, bis(cyclopentadienyl)-bis(2,6-difluoro-3-pyrryl-phenyl)titanium, trimethylbenzoyldiphenylphosphine oxide, bis(2,6-dimethoxy-benzoyl)-(2,4,4-trimethyl-pentyl)-phosphine oxide, bis(2,4,6-trimethylbenzoyl)-2,4-dipentyloxyphenyl-phosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds.

Further examples of additional photoinitiators are, for example, cationic photoinitiators, such as peroxide compounds, for example benzoyl peroxide (other suitable peroxides are described in U.S. Pat. No. 4,950,581, column 19, lines 17–25), aromatic sulfonium or iodonium salts, such as those to be found in U.S. Pat. No. 4,950,581, column 18, line 60 to column 19, line 10, or cyclopentadienyl-arene-iron(II) complex salts, for example ($\eta^6$-isopropylbenzene)-($\eta^5$-cyclopentadienyl)-iron(II) hexafluorophosphate.

The surface coatings may be solutions or dispersions of the surface-coating resin in an organic solvent or in water, but they may also be be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments, which may be inorganic or organic pigments, and metal powders for metal effect finishes.

The surface coatings may also comprise relatively small amounts of special additives customary in surface-coating technology, for example flow improvers, thixotropic agents, light stabilisers, antioxidants or sensitisers.

UV absorbers, such as those of the hydroxyphenyl-benzotriazole, hydroxyphenyl-benzophenone, oxalic acid amide or hydroxyphenyl-s-triazine type may be added as light stabilisers. Individual compounds or mixtures of those compounds can be used with or without the addition of sterically hindered amines (HALS).

Examples of such UV absorbers and light stabilisers are
1.2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyl-oxy)carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6- benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.

2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

4. Acrylates, such as α-cyano-β,β,-diphenylacrylic acid ethyl ester or isooctyl ester, α-carbo-methoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbo-methoxy-β-cyanovinyl)-2-methyl-indoline.

5. Sterically hindered amines, such as bis(2,2,6,6-tetramethyl-piperidyl)sebacate, bis-(2,2,6,6-tetramethyl-piperidyl)succinate, bis(1,2,2,6,6-pentamethylpiperidyl)sebacate, n-butyl-3,5-di-tert-butyl-4-hydroxybenzyl-malonic acid bis(1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethyl-enediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethyl-piperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis-(1-octyloxy-2,2,6,6-tetramethylpiperidyl)succinate, condensation product of N,N'-bis(2,2,6,6-tetra-methyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl- 1,3,8-triazaspiro[4.5]decane-2,4-dione, 3-dodecyl- 1-(2,2,6,6-tetramethyl-4-piperidyl) pyrrolidine-2,5-dione, 3-dodecyl-1-(1,2,2,6,6-pentamethyl-4-piperidyl)-pyrrolidine-2,5-dione.

6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyl-oxanilide and a mixture thereof with 2-ethoxy-2'-ethyl-5,4'-di-tert-butyl-oxanilide, mixtures of o- and p-methoxy- and of o- and p-ethoxy-disubstituted oxanilides.

7. 2-(2-HydroxyDhenyl)-1,3,5-triazines, such as 2,4,6-tris (2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl phenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecylo-/tridecyl-oxy-(2-hydroxypropyl)oxy-2-hydroxyphenyl]-4,6-bis(2,4-dimethylphenyl)-1,3,5-triazine.

8. Phosphites and phosphonites, such as triphenyl phosphite, diphenyl alkyl phosphites, phenyl dialkyl phosphites, tris(nonylphenyl) phosphite, trilauryl phosphite, trioctadecyl phosphite, distearyl-pentaerythritol diphosphite, tris(2,4-di-tert-butylphenyl) phosphite, diisodecylpentaerythritol diphosphite, bis(2,4-di-tert-butylphenyl)pentaerythritol diphosphite, bis(2,6-di-tert-butyl-4-methylphenyl) pentaerythritol diphosphite, bis-isodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228), 3-(aroylmethylene)-thiazolines, thioxanthones, condensed aromatic compounds, such as perylene, aromatic amines (as described, for example, in U.S. Pat. No. 4,069,954) or cationic and basic colourants (as described, for example, in U.S. Pat. No. 4,026,705), for example eosine, rhodanine and erythrosine colourants.

Other customary additives are—depending on the intended use—optical brighteners, fillers, pigments, colourants, wetting agents or flow improvers.

For curing thick and pigmented coatings, the addition of micro glass beads or powdered glass fibres, as described in U.S. Pat. No. 5,013,768, is suitable.

Other examples of additional photoinitiators or additives have been given hereinbefore.

Oximesulfonic acid esters can also be used, for example, in hybrid systems. Those systems are based on formulations that are full cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are, for example, radical full cure, oxidative crosslinking or humidity-initiated crosslinking. The second curing mechanism may be initiated purely thermally, if necessary with a suitable catalyst, or also by means of light using a second photoinitiator.

According to the invention, the photoactivatable compositions may comprise further photoinitiators, sensitisers and/or additives in addition to component c), or the compounds of formula I, Ia or Ib can be used together with further photoinitiators, sensitisers and/or additives.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP-A 245 639. The addition of redox initiators, such as cobalt salts, enables the curing to be assisted by oxidative crosslinking with oxygen from the air.

The surface coating can be applied by one of the methods customary in the art, for example by spraying, painting on or immersion. When suitable surface coatings are used, electrical application, for example by electroimmersion coating, is also possible. After drying, the surface coating film is irradiated. If necessary, the surface coating film is then fully cured by means of heat treatment.

The compounds of formulae I, Ia and Ib can also be used for curing mouldings made from composites. A composite consists of a self-supporting matrix material, for example a glass fibre fabric, impregnated with the photocuring formulation.

Resist systems can be prepared by image-wise irradiation of systems comprising compounds of formula I, Ia or Ib, followed by a developing step. As already mentioned above, compounds of formulae I, Ia and Ib can be used as photosensitive acid donors in a photoresist, especially for radiation at wavelengths over 390 nm.

The invention accordingly relates also to a photoresist for radiation at wavelengths over 390 nm based on oximesulfonates as photosensitive acid donors, the photoresist comprising as oximesulfonate a compound of formula I, Ia or Ib.

The difference in solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive. If, on the other hand, those components reduce the solubility of the composition after irradiation, the resist is negative.

The invention accordingly relates also to a negative photoresist and to a positive photoresist.

The oximesulfonic acid esters of formulae I, Ia and Ib can also be used in chemically amplified resists. A chemically amplified photoresist is understood to be a resist composition the photosensitive component of which, when irradiated, provides only that amount of acid that is required to catalyse a chemical reaction of at least one acid-sensitive component of the resist, as a result of which the ultimate differences in solubility between irradiated and non-irradiated areas of the photoresist first develop.

The invention accordingly relates also to a chemically amplified photoresist.

Such resists exhibit an outstanding lithographic sensitivity to long wavelength radiation, especially radiation over 390 nm. The photoresists according to the invention have excellent lithographic properties, especially a high sensitivity, and they also have the advantage that they function with radiation in the near UV range which is substantially easier to use from a technical standpoint. For example, the irradiation of large areas in particular is technically possible with long wavelength light.

Acid-sensitive components that produce a negative resist characteristic are especially compounds that, when catalysed by acid (the acid formed during irradiation of the compounds of formula I, Ia or Ib), are capable of undergoing a crosslinking reaction with themselves and/or with one or more further components of the composition. Compounds of that type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of that type are generally known and are described, for example, in Ullmann's Encyclopadie der technischen Chemie, 4th Edition, Vol. 15 (1978), p. 613–628. The crosslinker components should generally be present in a concentration of from 2 to 40, preferably from 5 to 30, percent by weight, based on the total solids content of the negative composition.

Especially preferred as acid-curable resins are amino resins, such as non-etherified or etherified melamine, urea, guanidine or biuret resins, especially methylated melamine resins or butylated melamine resins, corresponding glycolurils and urones. There are to be understood by resins in this context both customary technical mixtures, which generally also comprise oligomers, and pure and high purity compounds. N-Methoxymethyl melamine and tetramethoxymethyl glucoril and N,N'-dimethoxymethylurone are the acid-curable resins given the greatest preference.

The concentration of the compound of formula I, Ia or Ib in negative resists is in general from 0.1 to 30, preferably up to 20, percent by weight, likewise based on the total solids content of the compositions. From 1 to 15 percent by weight is especially preferred.

Where appropriate, the negative compositions may additionally comprise a film-forming polymeric binder. That binder is preferably an alkali-soluble phenolic resin. Well suited for that purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl) propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of those phenols with one or more ethylenically unsaturated materials, for example styrenes. The amount of binder should generally be from 30 to 95 percent by weight or, preferably, from 40 to 80 percent by weight.

The invention thus includes, as a special embodiment, as already mentioned above, negative, alkali-developable photoresists for a working radiation of a wavelength of more than 390 nanometers, comprising an oximesulfonate of formula I, Ia or Ib as described above, an alkali-soluble phenolic resin as binder and a component that when catalysed by an acid undergoes a crosslinking reaction with itself and/or with the binder.

An especially preferred form of that negative resist comprises from 1 to 15 percent by weight oximesulfonate, from 40 to 99 percent by weight of a phenolic resin as binder, for example one of those mentioned above, and from 0.5 to 30 percent by weight of a melamine resin as crosslinking agent, the percentages relating to the solids content of the composition. With novolak or especially with polyvinyl phenol as binder, a negative resist having especially good properties is obtained.

Oximesulfonic acid esters can also be used as photochemically activatable acid generators for the acid-catalysed crosslinking of, for example, poly(glycidyl)methacrylates in negative resist systems. Such crosslinking reactions are described, for example, by Chae et at in Pollimo 1993, 17(3), 292.

Monomeric or polymeric compounds that are alkali-insoluble but are cleaved in the presence of acid, or are capable of being rearranged intramolecularly, in such a manner that reaction products remain that are soluble in a customary alkaline developer and/or that cause an otherwise alkali-insoluble and acid-resistant additional binder to become soluble in the developer, produce a positive characteristic in photoresist compositions according to the invention. Substances of that type are referred to hereinafter as solution inhibitors.

As already indicated hereinbefore, the invention therefore includes, as a further special embodiment, positive alkaline-developable photoresists for a working radiation of a wavelength of more than 390 nanometers, comprising a compound of formula I, Ia or Ib and at least one compound that substantially prevents the composition from dissolving in an alkaline developer, but that can be cleaved in the presence of an acid in such a manner that reaction products remain that are soluble in the developer and/or that cause an acid-resistant additional binder that would otherwise be virtually insoluble in the developer to dissolve in the developer.

There may be used as solution inhibitors monomeric and polymeric organic compounds having functional groups that would be soluble per se in an alkaline medium, for example aromatic hydroxy groups, carboxylic acid groups, secondary amino groups and keto or aldehyde groups, but that have been chemically so altered by reaction with a suitable compound that they are insoluble in aqueous alkali, the protecting groups formed in the mentioned reaction being capable of being cleaved again by acid catalysis in such a manner that the functional groups are recovered in their original form.

For the protection of hydroxy groups, carboxylic acid groups or secondary amino groups there are suitable, for example, dihydrofuran or 3,4-dihydropyran and the derivatives thereof, benzyl halides, alkyl halides, haloacetic acid, haloacetic acid esters, chlorocarbonic acid esters, alkylsulfonyl halides, aromatic sulfonyl halides, dialkyl dicarbonates or trialkylsilyl halides, it being possible for the reactions to form the protected derivatives to be carried out in known manner. Customary conversion into ketals and acetals is suitable for protecting keto and aldehyde groups.

Such chemically amplified positive resist systems are described, for example, in E. Reich-manis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

In positive resists of the mentioned type a film-forming, polymeric solution inhibitor can either be the only binder in the photoresist or can be used in admixture with an acid-inert binder and, where appropriate, a monomeric solution inhibitor.

Examples of acid-inert binders are novolaks, especially those based on o-, m- or p-cresol and formaldehyde, also poly(p-hydroxystyrene), poly(p-hydroxy-α-methylstyrene) and copolymers of p-hydroxystyrene, p-hydroxy-α-methylstyrene and acetoxystyrene.

Examples of polymeric solution inhibitors are novolaks, especially those based on o-, m- or p-cresol and formaldehyde, poly(p-hydroxystyrene), poly(p-hydroxy-α-methylstyrene), copolymers of p-hydroxystyrene or p-hydroxy-α-methylstyrene and acetoxystyrene or acrylic acid and/or methacrylic acid and (meth)acrylic acid esters, which are reacted in known manner with dihydrofuran, 3,4-dihydropyran, benzyl halides, alkyl halides, haloacetic acid, haloacetic acid esters, chlorocarbonic acid esters, alkylsulfonyl halides, aromatic sulfonyl halides, dialkyl dicarbonate or trialkylsilyl halides. Also suitable are polymers of p-(2-tetra-hydropyranyl)-oxystyrene or p-(tert-butyloxycarbonyl)-oxystyrene with (meth)acrylic acid, (meth)acrylic acid esters and/or p-acetoxystyrene and polymers of p-hydroxystyrene and/or p-(2-tetrahydropyranyl)-oxystyrene with 3-hydroxybenzyl (meth)acrylates, which can, if necessary, additionally be protected by reaction with one of the compounds listed above.

Especially suitable are polymers that are transparent over a wavelength range of from 180 to 1000 nm and carry both groups that, after acid-catalysed deprotecting, bring about a change in solubility, and hydrophobic and hydrophilic groups that increase the solubility of the acid generator and ensure aqueous-alkaline developability. Examples of such polymers are acrylates and methacrylates prepared by co- or ter-polymerisation from the corresponding monomers. The monomers may also carry organosilicon radicals in order, for example, to increase the resistance in the case of dry etching processes. Examples of monomers are: methyl (meth)acrylate, (meth)acrylic acid, tert-butyl (meth)acrylate, trimethylsilylmethyl (meth)acrylate, 3-oxocyclohexyl (meth)acrylate, tetrahydropyranyl (meth)acrylate, adamantyl (meth)acrylate, cyclohexyl (meth)acrylate, norbornyl (meth)acrylate.

The invention accordingly also relates to a chemically amplified positive resist comprising as photosensitive acid donor a compound of formula I, Ia or Ib. Special preference is given to a chemically amplified positive resist comprising as photosensitive acid donor a compound of formula Ib.

The invention relates also to a photoresist comprising polymers that are transparent up to the wavelength region of 180 nm.

A special embodiment of the positive resist according to the invention comprises from 75 to 99.5 percent by weight of a film-forming polymer that contains protecting groups that can be removed by acid catalysis, and from 0.5 to 25 percent by weight of oximesulfonates of formula I, Ia or Ib, the percentages being based on the solids content of the compositions. In this context, preference is given to compositions comprising from 80 to 99 percent by weight of the mentioned polymer and from 1 to 20 percent by weight of oximesulfonate. Another embodiment is a positive resist comprising from 40 to 90 percent by weight of an acid-inert film-forming polymer as binder, from 5 to 40 percent by weight of a monomeric or polymeric compound having protecting groups removable by acid catalysis and from 0.5 to 25 percent by weight of oximesulfonates of formula I, Ia or Ib, the percentages relating to the solids content of the compositions. Of those compositions, preference is given to those comprising from 50 to 85 percent by weight acid-inert binder, from 10 to 30 percent by weight monomeric or polymeric solution inhibitor and from 1 to 15 percent by weight oximesulfonates.

Oximesulfonic acid esters can also be used as light-activatable solubility enhancers. In that case, the compounds are added to a film-forming material comprising substantially no components that polymerise with the oximesulfonic acid ester when heated or when irradiated with actinic radiation. However, the oximesulfonic acid esters reduce the speed at which the film-forming material dissolves in a suitable developer medium. That inhibiting effect can be cancelled by irradiating the mixture with actinic radiation, so that a positive image can be produced. Such an application is described, for example, in EP-A-241 423.

A further special embodiment of the invention is, finally, a positive resist comprising a compound of formula I, Ia or Ib and a binder that is virtually insoluble in an alkaline developer and that becomes soluble in the developer in the presence of the photolysis products of the compound of formula I, Ia or Ib. In this case the amount of the mentioned oximesulfonate compound is generally from 5 to 50 percent by weight, based on the solids content of the composition.

The use of the oximesulfonic acid esters according to the invention in chemically amplified systems, which operates on the principle of the removal of a protecting group from a polymer, generally produces a positive resist. Positive resists are preferred to negative resists in many applications, especially because of their greater resolution. There is, however, also interest in producing a negative image using the positive resist mechanism, in order to combine the advantages of the high degree of resolution of the positive resist with the properties of the negative resist. That can be achieved by introducing a so-called image-reversal step as described, for example, in EP-A-361 906. For that purpose, the image-wise irradiated resist material is treated, before the developing step, with, for example, a gaseous base, the acid that has been produced image-wise being neutralised. Then, a second irradiation, over its whole area, and thermal aftertreatment are carried out and the negative image is then developed in the customary manner.

In addition to the mentioned constituents, both the negative and the positive photoresist compositions may additionally comprise one or more of the additives customarily used in photoresists in the amounts familiar to a person skilled in the art, for example flow improvers, wetting agents, adhesives, thixotropic agents, colourants, pigments, fillers, solubility accelerators and so on. The reaction can be accelerated by the addition of photosensitisers which shift and/or broaden the spectral sensitivity. These are especially aromatic carbonyl compounds, such as benzophenone, thioxanthone, anthraquinone and 3-acylcoumarin derivatives and also 3-(aroylmethylene) thiazolines, but also eosine, rhodanine and erythrosine colourants.

For application, the compositions must generally also comprise a solvent. Examples of suitable solvents are ethyl acetate, 3-methoxymethyl propionate, ethyl pyruvate, 2-hepta-none, diethyl glycol dimethyl ether, cyclopentanone, cyclohexanone, γ-butyrolactone, ethyl methyl ketone, 2-ethoxyethanol, 2-ethoxyethyl acetate and especially 1-methoxy-2-propyl acetate. The solvent may also be in the form a mixture, for example of two or more of the above-mentioned solvents. The choice of solvent and the concentration depend, for example, on the nature of the composition and on the coating method.

The solution is uniformly applied to a substrate by means of known coating methods, for example by spin-coating, immersion, knife coating, curtain pouring techniques, brush application, spraying and reverse roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.1 $\mu$m to more than 100 $\mu$m.

Possible areas of use of the composition according to the invention are as follows: use as photoresists for electronics, such as etching resists, electroplating resists or solder resists, the manufacture of integrated circuits or thin film transistor-resist; TFT-resist, the manufacture of printing plates, such as offset printing plates or screen printing templates, use in the etching of mouldings or in stereolithography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

After the coating operation, the solvent is generally removed by heating, resulting in a layer of the photoresist on the substrate. The drying temperature must of course be lower than the temperature at which certain components of the resist might be thermally cured. Care must be taken in that respect especially in the case of negative photoresists. In general, drying temperatures should not exceed from 80 to 130° C.

The resist coating is then irradiated image-wise. The expression "image-wise irradiation" includes irradiation in a predetermined pattern using actinic radiation, i.e. both irradiation through a photomask containing a predetermined pattern, for example a transparency, and irradiation using a laser beam that is moved over the surface of the coated substrate, for example under the control of a computer, and thus produces an image.

After the irradiation and, if necessary, thermal treatment, the unirradiated sites (in the case of positive resists) or the irradiated sites (in the case of negative resists) of the composition are removed in a manner known per se using a developer.

It is generally necessary to allow a certain period of time prior to the developing step in order to allow the acid-sensitive components of the resist composition to react. In order to accelerate that reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 150° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may be used, for example, for the developing. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5N, but are usually diluted in suitable manner before use. For example solutions having a normality of approximately 0.1 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of those solvents. A typical aqueous/organic developer system is based on Butylcellosolve®/water.

It is known from EP-A-592 139 that oximesulfonic acid esters can be used as light-activatable acid generators in compositions that are suitable for the surface treatment and cleaning of glass, aluminium and steel surfaces. The use of those compounds in such organosilane systems results in compositions that have significantly better storage stability than those obtained when the free acid is used.

Oximesulfonic acid esters can also be used to produce so-called "print-out" images when the compound is used together with a colourant that changes colour when the pH changes, as described in Japanese Patent Application JP-A Hei 4 328 552 or in U.S. Pat. No. 5,237,059. Such colour-change systems can be used according to EP-A-199 672 also to monitor goods that are sensitive to heat or radiation.

In addition to a colour change, it is possible during the acid-catalysed deprotection of soluble pigment molecules for the pigment crystals to be precipitated; this can be used in the production of colour filters.

Suitable for the crosslinking of compositions comprising compounds of formula I, Ia or Ib are radiation sources that emit radiation of a wavelength of approximately from 180 to 1000, for example from 300 to 600 or preferably from 380 to 600, for example from 380 to 500, nanometers. Both point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the lamp and the substrate according to the invention to be irradiated can vary, for example, from 2 cm to 150 cm, according to the intended use and the type and/or strength of the lamp. Also suitable are laser light sources, for example excimer lasers, such as krypton-F lasers for irradiation at 248 nm or Ar-F lasers at 193 nm. Lasers in the visible range and in the infrared range can also be used. Very especially suitable is radiation of the mercury h and g lines at wavelengths of 436 and 405 nanometers. Suitable light sources are therefore especially mercury vapour lamps, especially medium and high pressure mercury lamps, from the radiation of which emission lines at other wavelengths can, if desired, be filtered out. That is especially the case for relatively short wavelength radiation. The distance between the lamp and the workpiece can vary, for example, from 2 cm to 150 cm, according to the intended use and the type and/or strength of the lamp. It is, however, also possible to use low energy lamps (for example fluorescent tubes) that are capable of emitting in the appropriate wavelength range. An example thereof is the Philips TL03 lamp. A suitable laser-beam source is, for example, the argon-ion laser, which emits radiation at wavelengths of 454, 458, 466, 472, 478 and 488 nanometers. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oximesulfonate in the composition in the irradiated sections of the surface coating decomposes to form sulfonic acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are especially suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures. The surface coating to be cured can be exposed directly to sunlight or daylight-equivalent light sources. The curing can, however, also take place behind a transparent layer (e.g. a pane of glass or a sheet of plastics).

The compounds of formulae I, Ia and Ib are generally added to the photoactivatable compositions in an amount of from 0.1 to 30% by weight, for example from 0.5 to 10% by weight, especially from 1 to 5% by weight.

The invention relates also to the use of compounds of formulae I, Ia and Ib as photosensitive acid donors for radiation at wavelengths over 390 nm in the preparation of surface coatings, printing inks, printing plates, dental compositions, colour filters, resist materials or image-recording materials, or image-recording materials for recording holographic images.

The Examples that follow further illustrate the invention. As in the remainder of the description and in the patent claims, unless otherwise indicated data in parts or percentages are based on the weight.

EXAMPLE 1

α-(Methylphenylsulfonyloxyimino)-3,4-dimethoxybenzyl cyanide 1.1: α-Hydroxyimino-3,4-dimethoxybenzyl cyanide 47 g (1.17 mol) of NaOH, dissolved in 450 ml of methanol, are added to 208.03 g (1.17 mol) of 3,4-dimethoxybenzyl cyanide in a sulfonating flask and the solution is cooled in an ice-bath to 0–5° C. At that temperature, with stirring for 4 hours, 1.17 mol of gaseous methyl nitrite (prepared in situ by the addition of 38 ml of conc. $H_2SO_4$, dissolved in 82 ml of water, to a solution of 97.1 g of $NaNO_2$ in 59 ml of water and 62 ml of methanol, see Org. Synthesis 59, 95, 1979) are introduced into the solution. The reaction solution is then stirred overnight and thereafter nitrogen is passed through the solution.

Methanol is distilled off in a rotary evaporator and the brown residue is then made into a slurry in a mixture of toluene and water for 30 minutes with stirring. The phases are separated and the aqueous phase is washed with toluene and then rendered acidic with concentrated HCl. The product is obtained in the form of a beige precipitate. The precipitate is filtered off, washed neutral with water, dried in vacuo and then recrystallised from ethyl acetate. 114 g (47%) of α-hydroxyimino-3,4-dimethoxybenzyl cyanide are obtained in the form of a beige solid having a melting point of 183–191° C. Elemental analysis: $C_{10}H_{10}N_2O_3$ (206.20)

|  | C [%] | H [%] | N [%] |
|---|---|---|---|
| calculated: | 58.25 | 4.89 | 13.59 |
| found: | 58.22 | 4.97 | 13.54 |

1.2: α-(4-Methylphenylsulfonyloxyimino)-3,4-dimethoxybenzyl cyanide 51.6 g (0.25 mol) of α-hydroxyimino-3,4-dimethoxybenzyl cyanide and 300 ml of triethylamine are dissolved in 300 ml of THF and cooled in an ice-bath to 0–5° C. There is added dropwise to that solution in the course of one hour a solution of 52.4 g (0.275 mol) of paratoluenesulfonic acid chloride in 65 ml of THF. After 3 hours the ice-bath is removed and the reaction mixture is then stirred overnight at room temperature. Then 150 ml of $CH_2Cl_2$ are added, the ammonium salts that have precipitated are filtered off and the filtrate is freed of excess triethylamine by repeated washing with water and dilute HCl. After drying over magnesium sulfate, the solvent is distilled off in a rotary evaporator and the residue that remains is recrystallised from toluene. 80.8 g (90%) of α-(4-methylphenylsulfonyloxyimino)-3,4-dimethoxybenzyl cyanide are obtained in the form of yellowish crystals having a melting point of 161–163° C. The $^1$H-NMR spectrum of the compound shows that it is a pure stereoisomer. The UV spectrum (acetonitrile) of the substance shows a broad absorption band with a maximum at 350 nm (ε=11340) that extends to 435 nm. Elemental analysis: $C_{17}H_{16}N_2O_5S$ (360.38)

|  | C [%] | H [%] | N [%] | S [%] |
|---|---|---|---|---|
| calculated: | 56.66 | 4.48 | 7.77 | 8.90 |
| found: | 56.76 | 4.55 | 7.71 | 8.89 |

EXAMPLE 2

α-(4-Methylsulfonyloxyimino)-3,4-dimethoxybenzyl cyanide

As described under 1.2., 14.4 g (0.07 mol) of α-hydroxyimino-3,4-dimethoxybenzyl cyanide are reacted with 8.8 g (0.077 mol) of methanesulfonyl chloride in the presence of triethylamine. GC analysis of the reaction mixture shows that a mixture of two isomers is formed in a ratio of 3:1. After recrystallisation from ethyl acetate, 12.0 g (60%) of α-(4-methylsulfonyloxyimino)-3,4-dimethoxybenzyl cyanide are obtained in the form of a yellow powder having a melting point of 140–146° C. The $^1$H-NMR spectrum shows the presence of a mixture of (E) and (Z) isomers in a ratio of 8:2. The isomeric mixture shows a UV/Vis spectrum (acetonitrile) with two absorption bands at 300 nm (ε=8400) and 337 nm (ε=10330) that extend to 430 nm. Elemental analysis: $C_{11}H_{12}N_2O_5S$ (284.29)

|  | C [%] | H [%] | N [%] | S [%] |
|---|---|---|---|---|
| calculated: | 46.47 | 4.25 | 9.85 | 11.28 |
| found: | 46.66 | 4.32 | 9.87 | 11.45 |

By means of flash chromatography of the product mixture (silica gel, eluant: petroleum ether/ethyl acetate 2:1), the (Z) isomer can be obtained in pure form. Yellow solid having a melting point of 152–158° C.

EXAMPLE 3

α-(4-Methylphenylsulfonyloxyimino)-4-thiomethylbenzyl cyanide 3.1: 4-Thiomethyl-benzyl alcohol methanesulfonate In a sulfonating flask, 50 g (0.32 mol) of 4-methylthiobenzyl alcohol and 46.3 g (0.32 mol) of methylsulfonyl chloride are dissolved in 250 ml of toluene and, with cooling at 10° C., 32.5 g (0.32 mol) of triethylamine are added dropwise. The reaction mixture is then heated to room temperature and stirred overnight. 400 ml of 2N hydrochloric acid are then added to the reaction solution slowly and with cooling. The phases are separated and the organic phase is washed with water, dried over $MgSO_4$ and concentrated in a rotary evaporator. 60 g (80%) of 4-methylthiobenzyl alcohol methanesulfonate are obtained in the form of a yellow oil.

3.2: 4-Methylthiobenzylnitrile 92.4 g (0.4 mol) of 4-methylthiobenzyl alcohol methanesulfonate are added at room temperature to a solution of 31.6 g (0.64 mol) of sodium cyanide in 300 ml of dimethyl sulfoxide and the solution is stirred overnight at room temperature. The solution is then poured into ice-water and the resulting solid is filtered off. The product is recrystallised from isopropanol/water (1:1). 56 g (87%) of 4-methylthiobenzylnitrile are obtained in the form of a colorless solid having a melting point of 44–44.5° C.

3.3: α-Hydroxyimino-4-methylthiobenzyl cyanide 10 g (0.06 mol) of methylthiobenzylnitrile are reacted as described under 1.1 with 0.06 mol of methyl nitrite. After working-up, 4.2 g (36%) of a-hydroxyimino-4-methylthiobenzyl cyanide are obtained in the form of a yellowish powder having a melting point of 132–133° C.

3.4: α-(4-Methylphenylsulfonyloxyimino)-4-thiomethylbenzyl cyanide 4 g (0.021 mol) of hydroxyimino-4-methylthiobenzyl cyanide are reacted in 25 ml of THF as described under 1.2, in the presence of 3.16 g (0.031 mol) of triethylamine, with 4.35 g (0.023 mol) of para-toluenesulfonic acid chloride. After working-up, 6.25 g (87%) of crude product are obtained in the form of a brownish solid. Recrystallisation from ethyl acetate yields 3.8 g of α-(4-methylphenylsulfonyloxyimino)-4-thiomethylbenzyl cyanide in the form of a yellowish solid having a melting point of 102–107° C. The $^1$H-NMR spectrum shows the presence of a mixture of (Z) and (E) isomers. The UV/Vis spectrum shows a band at 348 nm ($\epsilon$=18800) that extends to 440 nm. Elemental analysis: $C_{16}H_{14}N_2O_3S_2$ (346.4)

|  | C [%] | H [%] | N [%] | S [%] |
| --- | --- | --- | --- | --- |
| calculated: | 55.48 | 4.07 | 8.09 | 18.51 |
| found: | 55.33 | 4.09 | 7.87 | 18.75 |

EXAMPLE 4

α-(4-Dodecylphenylsulfonyloxyimino)-3,4-dimethoxybenzyl cyanide

Analogously to the preparation of Example 1, 14.4 g (0.07 mol) of α-hydroxyimino-3,4-dimethoxybenzyl cyanide are reacted at room temperature with 26.56 g (0.077 mol) of 4-dodecylbenzenesulfonyl chloride in 100 ml of tetrahydrofuran in the presence of 10.6 g (0.105 mol) of triethylamine. For working-up, the reaction mixture is poured into water and extracted several times with methylene chloride. After drying over magnesium sulfate, the solvent is distilled off in a rotary evaporator. The brown oil that remains is then purified by flash chromatography on silica gel (eluant: petroleum ether/ethyl acetate 3:1). 14.75 g (41%) of α-(4-dodecylphenylsulfonyloxyimino)-3,4-dimethoxybenzyl cyanide are obtained in the form of a viscous yellow oil. The $^1$H-NMR spectrum shows that it is the (syn) isomer. The UV/Vis spectrum (acetonitrile) shows an absorption band at 350 nm ($\epsilon$=10700) that extends to 435 nm. Elemental analysis: $C_{28}H_{38}N_2O_5S$

|  | C [%] | H [%] | N [%] | S [%] |
| --- | --- | --- | --- | --- |
| calculated: | 65.34 | 7.44 | 5.44 | 6.23 |
| found: | 64.87 | 7.36 | 5.49 | 6.14 |

EXAMPLE 5

α-(2-Propylsulfonyloxyimino)-3,4-dimethoxybenzyl cyanide

As described under 1.2, 16.5 g (0.08 mol) of α-hydroxyimino-3,4-dimethoxybenzyl cyanide are reacted with 12.6 g (0.088 mol) of 2-propanesulfonyl chloride in the presence of triethylamine. Recrystallisation of the crude product from ethyl acetate/hexane yields 21.9 g (88%) of α-(2-propylsulfonyloxyimino)-3,4-dimethoxybenzyl cyanide in the form of beige crystals having a melting point of 90.5–93.5° C. The $^1$H-NMR spectrum of the compound shows that it is a pure stereoisomer. The UV spectrum (acetonitrile) of the substance shows a broad absorption band with a maximum at 346 nm ($\epsilon$=1165034) that extends to 434 nm. Elemental analysis: $C_{13}H_{16}N_2O_5S$ (312.34)

|  | C [%] | H [%] | N [%] |
| --- | --- | --- | --- |
| calculated: | 49.99 | 5.16 | 8.97 |
| found: | 50.07 | 5.26 | 8.88 |

EXAMPLE 6

α-(2,4,6-Tris(isopropyl)phenylsulfonyloxyimino)-3,4-dimethoxybenzyl cyanide

As described under 1.2, 8.25 g (0.04 mol) of α-hydroxyimino-3,4-dimethoxybenzyl cyanide are reacted with 13.3 g (0.044 mol) of 2,4,6-tris(isopropyl)benzenesulfonyl chloride in the presence of triethylamine. After recrystallisation of the crude product from ethyl acetate/-hexane, 14.25 g (75%) of α-(2,4,6-tris(isopropyl)phenylsulfonyl-oxyimino)-3,4-dimethoxy-benzyl cyanide are obtained in the form of beige crystals having a melting point of 90.5–93.5° C. The $^1$H-NMR spectrum of the compound shows that it is a pure stereoisomer. The UV spectrum (acetonitrile) of the substance shows a broad absorption band with a maximum at 352 nm ($\epsilon$=11000) that extends to 433 nm. Elemental analysis: $C_{25}H_{32}N_2O_5S$ (472.6)

|  | C [%] | H [%] | N [%] |
| --- | --- | --- | --- |
| calculated: | 63.54 | 6.82 | 5.93 |
| found: | 63.44 | 6.72 | 5.81 |

EXAMPLE 7

α-(n-Octylsulfonyloxyimino)-3,4-dimethoxybenzyl cyanide

As described under 1.2, 10.3 g (0.05 mol) of α-hydroxyimino-3,4-dimethoxybenzyl cyanide are reacted with 11.7 g (0.055 mol) of 1-octanesulfonyl chloride in the presence of triethylamine. After recrystallisation of the crude product from ethyl acetate/hexane, 19.1 g (87%) of α-(n-octylsulfonyloxyimino)-3,4-dimethoxybenzyl cyanide are obtained in the form of beige crystals having a melting point of 72–75° C. The $^1$H-NMR spectrum of the compound shows that it is a pure stereoisomer. The UV spectrum (acetonitrile) of the substance shows a broad absorption band with a maximum at 349 nm ($\epsilon$=11330) that extends to 435 nm. Elemental analysis: $C_{18}H_{26}N_2O_5S$ (382.48)

|  | C [%] | H [%] | N [%] |
| --- | --- | --- | --- |
| calculated: | 56.53 | 6.85 | 7.32 |
| found: | 56.30 | 6.86 | 7.16 |

EXAMPLE 8

α-(4-Chlorophenylsulfonyloxyimino)-3,4-dimethoxybenzyl cyanide

As described under 1.2, 10.3 g (0.05 mol) of α-hydroxyimino-3,4-dimethoxybenzyl cyanide are reacted with 12.2 g (0.055 mol) of 4-chlorobenzenesulfonic acid chloride in the presence of triethylamine. After recrystallisation of the crude product from ethyl acetate/hexane, 15.9 g (84%) of α-(4-chlorophenyl-sulfonyloxyimino)-3,4-dimethoxybenzyl cyanide are obtained in the form of yellowish crystals having a melting point of 145.5–148.5° C. The $^1$H-NMR spectrum of the compound shows that it is a pure stereoisomer. The UV spectrum (acetonitrile) of the substance shows a broad absorption band with a maximum at 350 nm ($\epsilon$=11660) that extends to 437 nm. Elemental analysis: $C_{16}H_{13}ClN_2O_5S$ (380.80)

|  | C [%] | H [%] | N [%] | S [%] | Cl [%] |
|---|---|---|---|---|---|
| calculated: | 50.47 | 3.44 | 7.36 | 8.42 | 9.31 |
| foound: | 50.50 | 3.46 | 7.37 | 8.42 | 9.33 |

EXAMPLE 9

α-(Methylsulfonyloxyimino)-4-methylthiobenzyl cyanide

Analogously to the preparation of Example 3.4, 19.2 g (0.1 mol) of α-hydroxyimino-4-methyl-thiobenzyl cyanide are reacted, in the presence of 15.2 g (0.15 mol) of triethylamine, with 12.6 g (0.11 mol) of methanesulfonyl chloride. After working-up, there are obtained 22.8 g of beige crude product, which is recrystallised from 120 ml of ethyl acetate. 14.0 g (52%) of α-(methylsulfonyloxyimino)-4-methylthiobenzyl cyanide are obtained in the form of beige crystals having a melting point of 148–150° C. The $^1$H-NMR spectrum of the compound shows that it is a pure stereoisomer. The UV spectrum (acetonitrile) of the substance shows a broad absorption band with a maximum at 349 nm ($\epsilon$=14790) that extends to 440 nm. Elemental analysis: $C_{10}H_{10}N_2O_3S_2$ (270.30)

|  | C [%] | H [%] | N [%] | S [%] |
|---|---|---|---|---|
| calculated: | 44.43 | 3.73 | 10.36 | 23.72 |
| found: | 44.56 | 3.76 | 10.34 | 23.74 |

EXAMPLE 10

α-(4-Dodecylphenylsulfonyloxyimino)-4-methylthiobenzyl cyanide

Analogously to the preparation of Example 3.4, 10.6 g (0.55 mol) of α-hydroxyimino-4-methyl-thiobenzyl cyanide are reacted, in the presence of 8.35 g (0.0825 mol) of triethylamine, with 20.9 g (0.06 mol) of dodecylbenzenesulfonyl chloride. After working-up, a viscous brown-beige crude product is obtained which is purified by chromatography on silica gel (eluant: petroleum ether/ethyl acetate 20:1). 10.5 g (38%) of α-(4-dodecylphenylsulfonyloxyimino)-4-methylthiobenzyl cyanide are obtained in the form of a yellow-brown viscous liquid. The $^1$H-NMR spectrum of the compound shows that it is a pure stereoisomer. The UV spectrum (acetonitrile) of the substance shows a broad absorption band with a maximum at 351 nm ($\epsilon$=9750) that extends to 450 nm. Elemental analysis: $C_{27}H_{36}N_2O_3S_2$ (500.72)

|  | C [%] | H [%] | N [%] | S [%] |
|---|---|---|---|---|
| calculated: | 64.77 | 7.25 | 5.59 | 12.81 |
| found: | 64.72 | 7.29 | 5.58 | 12.76 |

EXAMPLE 11

9-(4-Methylphenylsulfonyloxyimino)-3,6-dimethoxyfluorene 11.1. 3,6-Dimethoxyfluoren-9-one.

3,6-Dimethoxyfluoren-9-one is prepared by the multistep synthesis described by C. Chuang et al. in J. Am. Chem. Soc. 1985, 107, 4238. According to that process, in the final synthesis step pure 3,6-dimethoxyfluoren-9-one is obtained which precipitates from the solution of the crude product. Yellowish crystals having a melting point of 139–144° C. (Literature: 142–144° C). That product is used in the subsequent reaction step without being further purified.

After concentration, a further yellowish solid having a melting point of 123–125° C. precipitates from the mother liquor. As described in the literature, that solid contains, in addition to 3,6-dimethoxyfluoren-9-one, also the isomeric compound 1,6-dimethoxyfluoren-9-one. It may be estimated from the $^1$H-NMR spectrum that the mixture is composed approximately of 55% 3,6-dimethoxyfluoren-9-one and 45% 1,6-dimethoxyfluoren-9-one. That isomeric mixture is also used in the subsequent reaction step without being further purified.

11.2. 9-Hydroxyimino-3,6-dimethoxyfluorene 4.7 g (0.0195 mol) of 3,6-dimethoxyfluoren-9-one and 2.7 g (0.039 mol) of hydroxylammonium chloride are heated at 90° C. in a mixture of 50 ml of ethanol and 20 ml of water. After five hours the solution is poured into ice/water and ethyl acetate is added. The resulting suspension is filtered and the product that has been filtered off is washed with water and dried in vacuo. 4.25 g (86%) of 9-hydroxyimino-3,6-dimethoxyfluorene are obtained in the form of a yellow solid having a melting point of 230–240° C. According to $^1$H-NMR, that crude product still contains amounts of 3,6-dimethoxyfluoren-9-one. The crude product is, however, used in the subsequent step without being further purified and 3,6-dimethoxyfluoren-9-one is not removed until the end product is purified. Elemental analysis: $C_{15}H_{13}NO_3$ (255.27)

|  | C [%] | H [%] | N [%] |
|---|---|---|---|
| calculated: | 70.58 | 5.13 | 5.49 |
| found: | 71.42 | 5.13 | 4.32 |

11.3. 9-(4-Methylphenylsulfonyloxyimino)-3,6-dimethoxyfluorene 3.8 g (0.015 mol) of 9-hydroxyimino-3,6-dimethoxyfluorene and 2.3 g (0.0225 mol) of triethylamine are suspended in 80 ml of tetrahydrofuran (THF) and, at 0° C., a solution of 3.1 g (0.0165 mol) of para-toluenesulfonic acid chloride in 20 ml of THF is added dropwise. After 4 hours, the ice-bath is removed and the reaction mixture is stirred overnight at room temperature. Then 40 ml of $CH_2Cl_2$ are added and the resulting ammonium salts are filtered off. The filtrate is washed with water and saturated NaCl, dried over magnesium sulfate and concentrated in a rotary evaporator. The resulting crude product is purified by flash chromatography on silica gel (eluant: petroleum ether/ ethyl acetate 2:1). The fraction containing the main product is taken up in 100 ml of hot ethanol and the solution is filtered while hot. On cooling, the product precipitates and is filtered off and dried in vacuo. 3.2 g (52%) of 9-(4-methylphenylsulfonyl-oxyimino)-3,6-dimethoxyfluorene are obtained in the form of yellow crystals having a melting point of 143–148° C. The UV spectrum (acetonitrile) of the substance shows absorption bands with a maximum at 314 nm ($\epsilon$=21100) that extend to 450 nm. Elemental analysis: $C_{22}H_{19}NO_5S$ (409.6)

|  | C [%] | H [%] | N [%] |
| --- | --- | --- | --- |
| calculated: | 64.53 | 4.68 | 3.42 |
| found: | 64.24 | 5.03 | 3.29 |

EXAMPLE 12

9-(4-Dodecylphenylsulfonyloxyimino)-3,6-dimethoxyfluorene

As described under 11.3., 5.1 g (0.02 mol) of 9-hydroxyimino-3,6-dimethoxyfluorene are reacted at 0° C., in the presence of 3.0 g (0.03 mol) of triethylamine in 100 ml THF, with 5.6 g (0.022 mol) of 4-dodecylbenzenesulfonyl chloride. The crude product obtained after isolation is purified by flash chromatography on silica gel (eluant: petroleum ether/ethyl acetate 4:1). 5.8 g (51.3%) of 9-(4-dodecyl-phenylsulfonyloxyimino)-3,6-dimethoxyfluorene are obtained in the form of a viscous yellow oil. The UV spectrum (acetonitrile) of the substance shows absorption bands with a maximum at 315 nm ($\epsilon$=21100) that extend to 443 nm. Elemental analysis: $C_{33}H_{41}NO_5S$ (563.76)

|  | C [%] | H [%] | N [%] | S [%] |
| --- | --- | --- | --- | --- |
| calculated: | 70.31 | 7.33 | 2.48 | 5.69 |
| found: | 70.10 | 7.42 | 2.52 |  |

EXAMPLE 13

Mixture of 9-(4-methylphenylsulfonyloxyimino)-3,6-dimethoxyfluorene and 9-(4-methylphenylsulfonyloxyimino)-1,6-dimethoxyfluorene 13.1. 9-Hydroxyimino-3,6-dimethoxyfluorene and 9-hydroxyimino-1,6-dimethoxyfluorene The mixture isolated from the mother liquor of Example 11.1, consisting of approx. 55% 3,6-dimethoxyfluoren-9-one and 45% 1,6-dimethoxyfluoren-9-one, is reacted analogously to the preparation described in Example 11.2 with hydroxylammonium chloride in ethanol/water. A beige solid is obtained which, according to $^1$H-NMR, is composed of approx. 75% 9-hydroxyimino-3,6-dimethoxyfluorene and 25% 9-hydroxyimino-1,6-dimethoxyfluorene. The crude product is used in the subsequent step without being further purified.

13.2. 9-(4-Methylphenylsulfonyloxyimino)-3,6-dimethoxyfluorene and 9-(4-methyl-phenyl-sulfonyloxyimino)-1,6-dimethoxyfluorene The crude product from Example 13.1. (8.9 g, 0.035 mol) is reacted analogously to Example 11.3 in 175 ml of THF at 0° C., in the presence of 5.3 g (0.0525 mol) of triethylamine, with 7.34 g (0.0385 mol) of para-toluenesulfonic acid chloride. The resulting ammonium salts are filtered off and the solution is washed with saturated sodium chloride solution, dried over magnesium sulfate and concentrated in a rotary evaporator. The crude product that precipitates is dissolved in hot ethyl acetate and filtered and hexane is added thereto. When the reaction mixture is left to stand, the product precipitates in the form of yellow-beige crystals of an isomeric mixture of 9-(4-methylphenylsulfonyloxyimino)-3,6-dimethoxyfluorene and 9-(4-methyl-phenylsulfonyloxyimino)-1,6-dimethoxyfluorene. The yield is 8.3 g (58%), and the melting point is 141–148° C. According to its $^1$H-NMR spectrum, the mixture is composed of approx. 70% 9-(4-methylphenylsulfonyloxyimino)-3,6-dimethoxyfluorene and 30% 9-(4-methyl-phenylsulfonyloxyimino)-1,6-dimethoxy-fluorene. The UV spectrum (acetonitrile) of the mixture shows absorption bands with a long wavelength maximum at 314 nm ($\epsilon$=18670) that extend to 440 nm. Elemental analysis: $C_{22}H_{19}NO_5S$ (409.6)

|  | C [%] | H [%] | N [%] | S [%] |
| --- | --- | --- | --- | --- |
| calculated: | 64.53 | 4.68 | 3.42 | 7.83 |
| found: | 64.26 | 4.70 | 3.49 | 7.66 |

EXAMPLE 14

Mixture of 9-(4-dodecylphenylsulfonyloxyimino)-3,6-dimethoxyfluorene and 9-(4-dodecylphenylsulfonyloxyimino)-1,6-dimethoxyfluorene As described in Example 13.2., 8.9 g (0.035 mol) of crude product from Example 13.1. are reacted in THF, in the presence of triethylamine, with 13.2 g (0.038 mol) of 4-dodecylbenzenesulfonyl chloride. The oil that is obtained as crude product is purified by flash chromatography twice on silica gel (eluant: petroleum ether/ethyl acetate 9:1, then petroleum ether/ethyl acetate 3:1). 13.0 g (66%) of a mixture of 9-(4-dodecylphenylsulfonyloxyimino)-3,6-dimethoxyfluorene and 9-(4-dodecylphenylsulfonyloxyimino)-1,6-dimethoxyfluorene are obtained in the form of a viscous reddish oil. According to its $^1$H-NMR spectrum, the mixture is composed of approx. 75% 9-(4-dodecylphenylsulfonyloxyimino)-3,6-dimethoxyfluorene and 25% 9-(4-dodecylphenylsulfonyloxyimino)-1,6-dimethoxyfluorene. The UV spectrum (acetonitrile) of the mixture shows absorption bands with a long wavelength maximum at 315 nm ($\epsilon$=18330) that extend to 445 nm. Elemental analysis: $C_{33}H_{41}NO_5S$ (563.76)

|  | C [%] | H [%] | N [%] | S [%] |
| --- | --- | --- | --- | --- |
| calculated: | 70.31 | 7.33 | 2.48 | 5.69 |
| found: | 70.31 | 7.37 | 2.47 | 5.37 |

EXAMPLE 15

α-(3-Trifluoromethylphenylsulfonyloxyimino)-3,4-dimethoxybenzyl cyanide

As described under 1.2., 4.1 g (0.02 mol) of a-hydroxyimino-3,4-dimethoxybenzyl cyanide are reacted with 5.4 g (0.022 mol) of 3-trifluoromethylphenylsulfonic acid chloride in the presence of triethylamine. After recrystallisation of the crude product from ethyl acetate/-hexane, 6.6 g (80%) of α-(3-trifluoromethyl-phenylsulfonyloxyimino)-3,4-dimethoxybenzyl cyanide are obtained in the form of yellowish crystals having a melting point of 129–130° C. The $^1$H-NMR spectrum of the compound shows that it is a pure stereoisomer. The UV spectrum (acetonitrile) of the substance shows a broad absorption band with a maximum at 351 nm ($\epsilon$=11700) that extends to 430 nm. Elemental analysis: $C_{17}H_{13}F_3N_2O_5S$ (414.36)

|  | C [%] | H [%] | N [%] | S [%] |
|---|---|---|---|---|
| calculated: | 49.28 | 3.16 | 6.76 | 7.74 |
| found: | 49.47 | 3.33 | 6.85 | 7.79 |

EXAMPLE 16

α-(Phenylsulfonyloxyimino)-3,4-dimethoxybenzyl cyanide

As described under 1.2., 10.3 g (0.05 mol) of a-hydroxyimino-3,4-dimethoxybenzyl cyanide are reacted with 9.71 g (0.055 mol) of 4-benzenesulfonic acid chloride in the presence of 7.6 g of triethylamine. After recrystallisation of the crude product from ethyl acetate/hexane, 11.1 g (64%) of α-(phenyl-sulfonyloxyimino)-3,4-dimethoxybenzyl cyanide are obtained in the form of yellowish crystals having a melting point of 138.5–142° C. The $^1$H-NMR spectrum of the compound shows that it is a pure stereoisomer. The UV spectrum (acetonitrile) of the substance shows a broad absorption band with a maximum at 350 nm ($\epsilon$=11370) that extends to 436 nm. Elemental analysis: $C_{16}H_{14}N_2O_5S$ (346.36)

|  | C [%] | H [%] | N [%] | S [%] |
|---|---|---|---|---|
| calculated: | 55.48 | 4.07 | 8.03 | 9.29 |
| found: | 55.51 | 4.12 | 8.10 | 9.28 |

By evaporation of the mother liquor 2.6 g of a beige substance with a melting point of 104–110° C. are obtained, which by $^1$H-NMR-analysis is identified as a mixture of the (Z)- and (E)-isomers of α-(phenyl-sulfonyloxyimino)-3,4-dimethoxybenzyl cyanide (ratio ca. 2:1).

EXAMPLE 17

α-(4-Methoxyphenylsulfonyloxyimino)-3,4-dimethoxybenzyl cyanide

As described under 1.2., 10.3 g (0.05 mol) of α-hydroxyimino-3,4-dimethoxybenzyl cyanide are reacted with 11.37 g (0.055 mol) of 4-methoxyphenylsulfonic acid chloride in the presence of 7.6 g of triethylamine. After recrystallisation of the crude product from ethyl acetate/hexane, 3.26 g (17%) of α-(4-methoxy-phenylsulfonyloxyimino)-3,4-dimethoxybenzyl cyanide are obtained in the form of yellowish crystals having a melting point of 161–167° C. The $^1$H-NMR spectrum of the compound shows that it is a pure stereoisomer. The UV spectrum (acetonitrile) of the substance shows a broad absorption band with a maximum at 349 nm ($\epsilon$=11700) that extends to 435 nm. Elemental analysis: $C_{17}H_{16}N_2O_6S$ (376.38)

|  | C [%] | H [%] | N [%] | S [%] |
|---|---|---|---|---|
| calculated: | 54.25 | 4.28 | 7.44 | 8.52 |
| found: | 54.16 | 4.23 | 7.35 | 8.47 |

EXAMPLE 18

α-(4-Nitrophenylsulfonyloxyimino)-3,4-dimethoxybenzylcyanid

According to the method described under 1.2 α-Hydroxyimino-3,4-di-methoxybenzylcyanid and 4-Nitrophenylsulfonsaurechlorid are reacted. The physical data are given in table A

EXAMPLE 19

9-(n-Octylsulfonyloxyimino)-3,6-dimethoxyfluorene

As described under 11.3., 2.55 g (0.01 mol) of 9-hydroxyimino-3,6-dimethoxyfluorene are reacted at 0° C., in the presence of 1.5 g (0.015 mol) of triethylamine in 60 ml of THF, with 2.34 g (0.011 mol) of n-octylsulfonyl chloride. The crude product obtained after isolation is purified by recrystallisation from acetic acid acetate. 2.2 g (51%) of yellow-beige crystals of 9-(n-octyl-sulfonyloxyimino)-3,6-dimethoxyfluorene having a melting point of 105–110° C. are obtained. The UV spectrum (acetonitrile) of the substance shows a broad absorption band with a maximum at 313 nm ($\epsilon$=20620) that extends to 445 nm. Elemental analysis: $C_{23}H_{29}NO_5S$ (431.55)

|  | C [%] | H [%] | N [%] | S [%] |
|---|---|---|---|---|
| calculated: | 64.01 | 6.77 | 3.25 | 7.43 |
| found: | 63.90 | 6.80 | 3.40 | 7.28 |

EXAMPLE 20

α-(2-Propylsulfonyloxyimino)-4-methylthiobenzyl cyanide

Analogously to the preparation of Example 3.4, 9.6 g (0.5 mol) of α-hydroxyimino-4-methylthiobenzyl cyanide are reacted, in the presence of 7.6 g (0.075 mol) of triethylamine, with 7.85 g (0.055 mol) of 2-propanesulfonyl chloride. After working-up, the crude product is recrystallised from acetic acid acetate/hexane. 11.1 g (83%) of α-(2-propylsulfonyloxyimino)-4-methylthiobenzyl cyanide are obtained in the form of beige crystals having a melting point of 83–87° C. The $^1$H-NMR spectrum of the compound shows that it is a pure stereoisomer. The UV spectrum (acetonitrile) of the substance shows a broad absorption band with a maximum at 350 nm ($\epsilon$=14660) that extends to 435 nm. Elemental analysis: $C_{12}H_{14}N_2O_3S_2$ (266.32)

|  | C [%] | H [%] | N [%] | S [%] |
|---|---|---|---|---|
| calculated: | 48.30 | 4.72 | 9.38 | 21.49 |
| found: | 48.19 | 4.79 | 9.50 | 21.85 |

EXAMPLE 21

α-(4-Methylphenylsulfonyloxyimino)-3,4-bis (methylthio)benzyl cyanide 21.1. 1,2-Bis(methylthio)benzene 1,2-Bis(methylthio)benzene is prepared from thiophenol in accordance with the procedure of M. Dötze et al, Phosphorus, Sulfur, and Silicon 1993, 84, 95. It is a yellowish oil having a boiling point of 154° C./22 mbar and is obtained in a yield of 29%.

21.2. 1,2-Bis(methylthio)-4-chloromethyl-benzene 46 g (0.343 mol) of $AlCl_3$ are suspended in 200 ml of 1,2-dichloroethane and, at 0° C., 9.1 g (0.12 mol) of formaldehyde dimethylacetal are added. Then 17.0 g (0.1 mol) of 1,2-bis-(methylthio)benzene are added dropwise and the suspension is heated to room temperature. When the starting material can no longer be detected by GC analysis, the solution is poured into ice/water and the organic phase is separated off and dried over magnesium sulfate. When the solvent has been distilled off, 12.1 g (55%) of 1,2-bis (methylthio)-4-chloromethyl-benzene are obtained in the form of a yellow oil. The $^1$H-NMR spectrum ($CDCl_3$) of the compound is consistent with the suggested structure: 7.17–7.13, s and d, 3 aromatic H; 4.52, s, 2H; 2.44, s, $CH_3S$ and 2.43, s, $CH_3S$.

21.3. 3,4-Bis(methylthio)benzyl cyanide 42.5 g (0.194 mol) of 1,2-bis(methylthio)-4-chloromethyl-benzene and 25.3 g (0.388 mol) of potassium cyanide are stirred at ambient temperature in 200 ml of DMSO. When the starting material can no longer be detected by GC analysis, the brown solution is poured into ice/water and extracted with acetic acid acetate and the organic phase is dried over magnesium sulfate. After evaporation 34.8 g (85.7%) of 3,4-bis(methylthio)-benzyl cyanide are obtained as brown substance. The $^1$H-NMR-spektra data ($CDCl_3$) are in accordance with the proposed structure of the compound: 7.24–7.06 ppm (s and d, 3 aromatic H), 3.70 ppm (s, 2H), 2.47 ppm (s, $CH_3S$) and 2.45 ppm (2 s, $CH_3S$).

21.4. α-Hydroxyimino-3,4-bis(methylthio)benzyl cyanide

According to the method described under 1.1., 34.8 g (0.166 mol) of 3,4-bis(methylthio)benzyl cyanide are reacted with 0.166 mol methylnitrite. After the isolation 23.0 g (58%) α-hydroxyimino-3,4-bis(methylthio)benzyl cyanide are obtained as a brown substance with a melting point of 131–133° C. Elemental analysis: $C_{10}H_{10}N_2OS_2$ (238.33)

|             | C [%] | H [%] | N [%] | S [%] |
|-------------|-------|-------|-------|-------|
| calculated: | 50.40 | 4.23  | 11.75 | 26.90 |
| found:      | 50.52 | 4.17  | 11.49 | 26.82 |

21.5 α-(4-Methylphenylsulfonyloxyimino)-3,4-dithiomethylbenzyl cyanide

According to the method described under 1.2, 10.0 g (0.042 mol) of α-hydroxyimino-3,4-bis(methylthio)benzyl cyanide are reacted with 8.8 g (0.046 mol) of para-toluenesulfonic acid chloride in the presence of triethylamine. After recrystallisation from toluene 10.5 g (64%) of α-(4-methylphenylsulfonyloxyimino)-3,4-dithiomethylbenzyl cyanide are obtained as yellowish crystals melting at 155–157° C. The UV spectrum (acetonitrile) of the substance shows a broad absorption band with a maximum at 343 nm (ε=10710) that extends to 476 nm.

EXAMPLE 22

α-(Methylsulfonyloxyimino)-3,4-dithiomethylbenzylcyanid

According to the method described under 1.2 α-Hydroxyimino-3,4-bis(methylthio)benzyl cyanide are reacted with 6.9 g (0.06 mol) methansulfonyl chloride The physical data are given in table A.

EXAMPLE 23

9-(4-Dodecylphenyisulfonyloxyimino)-3,6-di(4-hydroxyethylthio)fluorene 23.1. 3,6-Difluorofluoren-9-one 3,6-Difluorofluoren-9-one is prepared in accordance with the multi-step synthesis described by N. Balasubramanian et al. in J. Bioorg. Med. Chem. Lett. 1991, 2, 99.

23.2. 3,6-Di(4-hydroxyethylthio)fluoren-9-one 10.8 g (0.05 mol) of 3,6-difluorofluoren-9-one, 9.4 g (0.12 mol) of 2-mercaptoethanol and 27.65 g of potassium carbonate are heated in 130 ml of N,N-dimethylacetamide at 90° C. for six hours. After cooling, the reaction mixture is diluted with water, the aqueous phase is extracted with ethyl acetate and the extracts are dried over magnesium sulfate. The solvent is evaporated off and the viscous red oil that is obtained is purified by chromatography on silica gel (eluant: ethyl acetate). 3.5 g (21%) of 3,6-di(4-hydroxyethylthio) fluoren-9-one are obtained in the form of an orange solid. The $^1$H-NMR spectrum is consistent with the suggested structure.

23.3. 9-Hydroxyimino-3,6-di(4-hydroxyethylthio)fluorene 4.8 g (0.014 mol) of 3,6-di(4-hydroxyethylthio)fluoren-9-one and 2 g (0.0288 mol) of hydroxylammonium chloride are heated under reflux in 25 ml of ethanol and 10 ml of water for three hours. The reaction mixture is then poured into ice-water, extracted with ethyl acetate and dried. After concentration by evaporation, 4.4 g (90%) of 9-hydroxyimino- 3,6-3,6-di(4-hydroxyethylthio)fluorene are obtained in the form of a yellow solid. The $^1$H-NMR spectrum is consistent with the suggested structure.

23.4.1 9-(4-Dodecylphenylsulfonyoxyimino 4)-3,-di4-hydroxyethelthio)fluorere 3.8 g (0.011 mol) of 9-hydroxyimino-3,6-3,6-di(4-hydroxyethylthio)fluorene and 1.67 g (0.0165 mol) of triethylamine are dissolved in 60 ml of $CH_2C_{12}$ and, at 0° C., 4.1 g (0.012 mol) of 4-dodecylphenylsulfonyl chloride are added dropwise. The reaction mixture is stirred overnight at room temperature and then the resulting ammonium salts are filtered off. After drying over magnesium sulfate, the residue is chromatographed on silica gel (eluant: ethyl acetate). A fraction of a red viscous oil is isolated which, according to the $^1$H-NMR s pectrum, has the structure of 9-(4-dodecylphenylsulfonyloxyimino)-3,6-di(4-hydroxyethylthio)fluorene. Elemental analysis: $C_{35}H_{45}NO_5S_3$ (655.94)

|             | C [%] | H [%] | N [%] | S [%] |
|-------------|-------|-------|-------|-------|
| calculated: | 64.09 | 6.92  | 2.14  | 14.60 |
| found:      | 63.78 | 7.11  | 1.74  | 13.89 |

EXAMPLE 24

3-(para-Cyano-1-[4-dodecylphenylsulfonyloxyimino]-benzyl)-5,7-dibutoxy coumarin 24.1. 3-(para-Cyano-1-[hydroxyimino]-benzyl)-5,7-dibutoxy-coumarin 3.9 g (0.01 mol) of 3-(par a-cyanobenzoyl)-5,7-d ibutoxy-coumarin (prepared in accordance with D. P. Specht et al., Tetrahedron 1982, 38, 1203) and 1.4 g (0.02 mol) of hydroxylammonium chloride are heated under reflux for 12 hours in a mixture of 50 ml of ethanol and 20 ml of water. After cooling, the reaction mixture is poured into ice/water, the phases are separated and the aqueous phase is extracted twice with ethyl acetate. After drying and evaporating off the solvent, 4.4 g of an orange crude product are obtained which, according to $^1$H-NMR, contains 3-(para-cyano-1-[hydroxyimino]-benzyl)-5,7-dibutoxy-coumarin as main product. That crude product is used in the subsequent step without being further purified.

24.2. 3-(para-Cyano-1-[4-dodecylphenylsulfonyloxyimino]-benzyl)-5,7-dibutoxy-coumarin 4.4 g (0.011 mol) of 3-(para-cyano-1-[hydroxyimino]-benzyl)-5,7-dibutoxy-coumann are reacted with 4.1 g (0.0118 mol) of 4-dodecylphenylsulfonyl chloride in the presence of 1.64 g (0.01h6 mol) of triethylamine analogously to Example 1.2. A very viscous crude product is obtained, which is suoended in hexane and acetic acid acetate. The precipitated substance is filtrated and the mother liquor evaporated. 2.3 g (1w7%) of 3-(para-cyano-1-[4-dodecylphenylsuffonyloxyimino]-benzyl)-5,7-dibutoxy-coumarin as red resin are obtained. Elemental analysis: $C_{41}H_{50}N_2O_7S$ (714.91)

|  | C [%] | H [%] | N [%] | S [%] |
|---|---|---|---|---|
| berechnet: | 68.88 | 7.05 | 3.92 | 4.48 |
| gefunden: | 68.69 | 7.96 | 4.28 | 4.55 |

EXAMPLES 25–30

The compounds of the examples 25 to 30 are obtained according to the method described under 1.2 by reacting the corresponding educts. The structures and physical data are listed in table A.

TABLE A

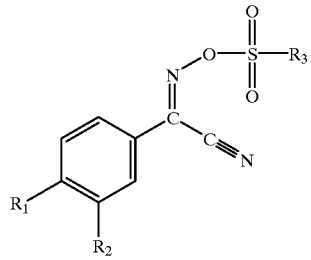

| Example | R$_1$ | R$_2$ | R$_3$ | yield | description/ melting point. |
|---|---|---|---|---|---|
| 18 | CH$_3$O | CH$_3$O | —⟨⟩—NO$_2$ | 35% | beige crystals, mp. 149–151° C. (decomposition) |
| 22 | CH$_3$S | CH$_3$S | CH$_3$ | 74% | yellow crystals, mp. 164–165° C. |
| 25 | CH$_3$O | CH$_3$O | H$_3$C-⟨⟩-CH$_3$ (with H$_3$C) | 69% | yellowish crystals, mp. 149–152° C. |
| 26 | CH$_3$S | CH$_3$O | —⟨⟩—CH$_3$ | 52% | yellowish crystals, mp. 139–142° C. |
| 27 | CH$_3$S | CH$_3$O | CH$_3$ | 62% | yellowish crystals, mp. 162–164° C. |

TABLE A-continued

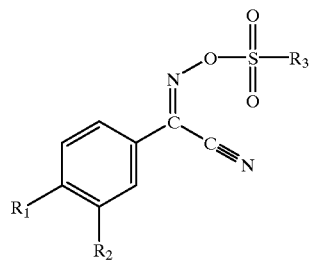

| Example | $R_1$ | $R_2$ | $R_3$ | yield | description/ melting point. |
|---|---|---|---|---|---|
| 28 | $CH_3S$ | H | 3-CF$_3$-phenyl | 30% | yellowish crystals, mp. 118–122° C. |
| 29 | $CH_3S$ | H | 4-NO$_2$-phenyl | 41% | orange-yellow crystals, mp. 167–168° C. (decomposition) |
| 30 | $CH_3S$ | H | 4-Cl-phenyl | 33% | yellowish crystals, mp. 160–165° C. |

EXAMPLE 31

Preparation of a Photoresist

A resist solution is prepared by mixing 65 parts of polyvinyl phenol (Mw=22 000 Polyscience), 30 parts of hexa(methoxymethyl)melamine (Cymel®303, cyanamide) and 5 parts of the test compound and dissolving 2.5 g of this mixture in 7.5 g of 1-methoxy-2-propyl acetate containing 1000 ppm of a flow assistant (FC$_{430}$). The solution is applied by spin coating for 30 s at 5000 rev/min to the polished and hexamethyidisilazane-treated side of silicon wafers having a diameter of 10.2 cm (4 inches). This results in a thickness of the coating of 1 µm. The solvent is removed by drying the coated wafer on a hotplate at 110° C. for 60 seconds. The samples thus obtained are irradiated image-wise through a mask with areas of different grey scales, using interference filters that are selectively permeable to light of wavelengths of 365 nm, 405 nm or 436 nm (Canon PLA 501, mercury high-pressure lamp). The wafers are then heated at 110° C. for 60 seconds in order to effect crosslinking in the irradiated areas, catalysed by the acid released by the irradiation. Developing is then carried out for 60 seconds in a 2.8% solution of tetramethylammonium hydroxide. The radiation dose that is required to achieve a film thickness after developing that corresponds to the thickness before developing is determined. The measurement of the film thickness is carried out using a Zeiss Axiotron (white-light interference). The lower the radiation dose required, the more reactive is the latent photohardener.

The results are listed in Table 1. The results show that using the photohardeners according to the invention, negative resists having a high degree of sensitivity are obtained.

TABLE 1

| Photohardener from Example | Sensitivity at 365 nm [mJ/cm$^2$] | Film thickness [nm] |
|---|---|---|
| 1 | 10 | 1090 |
| 2 (E/Z mixture) | <6 | 1080 |
| 2 (Z isomer) | 10 | 1080 |
| 3 | <6 | 1100 |
| 4 | <6 | 1100 |

By irradiation with light of the wavelength 405nm or 436 nm an image is obtained as well.

EXAMPLE 32

Preparation of a positive resist a) The preparation of the binder polymer is effected analogously to K. Nakano et al., Proc. SPIE, 2438, 433–39 (1995): terpolymer of methacrylic acid tetrahydro-2H-pyranyl ester, methacrylic acid and methyl methacrylate.

In a 250 ml round-bottomed flask, a solution of 8.51 g (50 mmol) of methacrylic acid tetra-hydro-2H-pyranyl ester, 4.0 g (40 mmol) of methyl methacrylate, 0.86 g (10 mmol) of methacrylic acid and 0.32 g of azo-bisisobutyronitrile in 100 ml of tetrahydrofuran is stirred for 20 hours at 75° C. under a nitrogen atmosphere. The reaction solution is cooled and then precipitated from 1 litre of n-hexane. The precipitate that forms is filtered off and dried under a high vacuum (4×10$^{-6}$ bar), 11.4 g (85% of the theoretical yield) of a white powder being obtained.

GPC (polystyrene calibration): Mn=7 100, Mw=19 500, PD=2.7

TGA (10° C./min): weight loss of 32% between 110–210° C.

b) Preparation of a positive i-line resist

A resist solution is prepared by dissolving 0.98 g of the polymer from Preparation example a) and 20 mg of the photohardener from Example 3 in 4 g of 1-methoxy-2-propyl acetate. The solution is applied by spin coating at 3000 rev/min to a silicon wafer having a diameter of 7.65 cm (3 inches). Subsequent drying at 100° C. for 1 min yields a film having a coating thickness of 1.0 micrometer. That film is irradiated image-wise using a mercury vapour lamp of the Ushio UXM-502 MD type through a narrow band interference filter and a chromium/quartz mask at 365 nm at a dose of 5 mJ/cm². The wafer is then heated on the hotplate for one minute at 100° C. and then developed in a 0.033N solution of tetramethylammonium hydroxide in water, the previously irradiated zones of the resist film dissolving, but the non-irradiated zones remaining. Positive patterns of the mask are obtained with good resolution.

EXAMPLE 33

A resist solution is prepared by mixing 65 parts of polyvinyl phenol (Mw=5 000, Maruzen Chemicals), 30 parts of hexa(methoxymethyl)melamine (Cymel®303, Cyanamide) and 5 parts of the test compound and dissolving 2.5 g of this mixture in 7.5 g of 1-methoxy-2-propyl acetate containing 1000 ppm of a flow assistant ($FC_{430}$, 3M Company). The solution is applied by spin coating for 30 s at 5000 rev/min to the polished and hexamethyldisilazane-treated side of silicon wafers having a diameter of 10.2 cm (4 inches). This results in a thickness of the coating of 1 μm. The solvent is removed by drying the coated wafer on a hotplate at 110° C. for 60 seconds. The samples thus obtained are irradiated image-wise through a mask with areas of different grey scales, using interference filters that are selectively permeable to light of wavelengths of 365 nm, 405 nm or 436 nm (Canon PLA 501, mercury high-pressure lamp). The wafers are then heated at 110° C. for 60 seconds in order to effect crosslinking in the irradiated areas, catalysed by the acid released by the irradiation. Developing is then carried out for 60 seconds in a 2.8% solution of tetramethylammonium hydroxide. The radiation dose that is required to achieve a film thickness after developing that corresponds to the thickness before developing is determined. The measurement of the film thickness is carried out using a Zeiss Axiotron (white-light interference). The lower the radiation dose required, the more reactive is the latent photohardener. The results are listed in Table 2. The results show that using the photohardeners according to the invention, negative resists having a high degree of sensitivity are obtained.

TABLE 2

| Photohardener from Example | Sensitivity at 365 nm [mJ/cm²] | Film thickness [nm] |
|---|---|---|
| 15 | 5 | 960 |
| 16 | 7 | 995 |

By irradiation with light of the wavelength 405 nm or 436 nm an image is obtained as well. With the compounds of examples 11 and 17 images at the corresponding wavelengths are obtained, too.

What is claimed is:

1. A photoactivatable composition comprising
a) at least one compound that can be crosslinked under the action of an acid and/or
b) at least one compound the solubility of which is altered under the action of an acid and
c) as photoinitiator, at least one compound of formula I

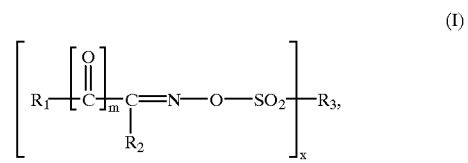

m is 0 or 1 and x is 1 or 2;

$R_1$ is phenyl substituted by one or more of the radicals $OR_4$ and/or $SR_4$ it being possible for the substituents $OR_4$ and $SR_4$ to form 5- or 6-membered rings, via the radicals $R_4$ or with one of the carbon atoms of the phenyl ring, with the proviso that when the phenyl ring is substituted by methoxy at least one further substituent must be present on the ring, or $R_1$ is naphthyl, anthracyl or phenanthryl, the radicals naphthyl, anthracyl and phenanthryl being substituted by OR4 and/or $SR_4$, it being possible for the substituents OR4 and $SR_4$ to form 5- or 6-membered rings, via the radicals $R_4$, or with one of the carbon atoms of the naphthyl, anthracyl or phenanthryl ring, or $R_1$ is a heteroaryl radical that is substituted by $OR_4$ and/or $SR_4$ it being possible for the substituents $OR_4$ and $SR_4$ to form 5- or 6-membered rings, via the radicals $R_4$, or with one of the carbon atoms of the heteroaryl ring, $R_2$ is $C_2$–$C_6$alkoxycarbonyl, CN, $C_1$–$C_4$haloalkyl, $S(O)_nC_1$–$C_6$alkyl, or unsubstituted or $C_1$–$C_{12}$alkyl-substituted $S(O)n$-$C_6$–$C_{12}$aryl, wherein n is 1 or 2; or $R_1$ and $R_2$, if appropriate together with the CO group, form a 5- or 6-membered ring that is substituted by $OR_4$ or $SR_4$ and that may additionally be interrupted by 0, S, $NR_5$ and/or by CO and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or substituted by one or more of the radicals halogen, $C_1$–$C_4$haloalkyl, CN, $NO_2$, $C_1$–$C_{16}$alkyl, phenyl, $OR_4$, $COOR_7$, —OCO—$C_1$–$C_4$alkyl, $SO_2OR_7$ and/or by $R_5R_6N$, or $R_3$, when x is 2, is $C_2$–$C_{12}$alkylene, phenylene, naphthylene,

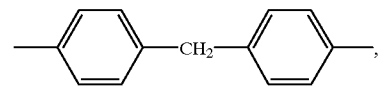

diphenylene or oxydiphenylene, the radicals phenylene, naphthylene,

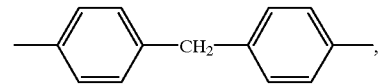

diphenylene and oxydiphenylene being unsubstituted or substituted by $C_1$–$C_{12}$alkyl;

$R_4$ is hydrogen, $C_1$–$C_{12}$alkyl that is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—, or $R_4$ is phenyl;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring which may be interrupted by —O— or by —$NR_4$—; and $R_7$ is $C_1$–$C_{12}$alkyl that is unsubstituted or substituted by OH and/or by $C_1$–$C_4$alkoxy and that may additionally be interrupted by —O—.

2. A composition according to claim 1, wherein in the compound of formula I $R_4$ is $C_1$–$C_6$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—.

3. A composition according to claim 1, wherein in the compound of formula I m is 0 and x is 1.

4. A composition according to claim 3, wherein in the compound of formula I $R_3$ is $C_1$–$C_{18}$alkyl, $C_1$–$C_{10}$haloalkyl, or phenyl that is unsubstituted or substituted by halogen, $NO_2$, $C_1$–$C_4$haloalkyl, $C_1$–$C_{12}$alkyl, $OR_4$, $COOR_7$ and/or by —OCO—$C_1$–$C_4$alkyl.

5. A composition according to claim 1, wherein in the compound of formula I m is 0 and x is 1, $R_1$ is 3,4-dimethoxyphenyl, 3,4-di(methylthio)phenyl, 3-methoxy-4methylthiophenyl or 4-methylthiophenyl, $R_2$ is CN, and $R_3$ is phenyl, 4-methylphenyl, 4-methoxyphenyl, 3-trifluoromethylphenyl, 4-chlorophenyl, methyl, isopropyl, n-octyl, 2,4,6-(triisopropyl)-phenyl 4-nitrophenyl, 2,4,6-trimethylphenyl or 4-dodecylphenyl, or $R_1$ and $R_2$ together form a fluorene system in which the aromatic rings are substituted by methoxy or hydroxyethylthio groups.

6. A composition according to claim 1 which comprises in addition to component c) further photoinitiators, sensitisers and/or additives.

7. A method of crosslinking compounds that can be crosslinked under the action of an acid, which method comprises adding a compound of formula I according to claim 1 to the above-mentioned compounds and irradiating image-wise or over the whole area with light having a wavelength of 180–600 nm.

8. A process for the preparation of surface coatings, printing inks, printing plates, dental compositions, colour filters, resist materials and image-recording material, wherein a composition according to claim 1 is employed, and irradiated with light.

9. A composition according to claim 1, wherein in the compound of formula I, $R_1$ is phenyl substituted by $OR_4$ and/or $SR_4$, it being possible for the substituents $OR_4$ and $SR_4$ to form 5- or 6-membered rings, via the radicals $R_4$ or with one of the carbon atoms of the phenyl ring.

10. A composition according to claim 1, wherein in the compound of formula I, $R_1$ is a heteroaryl radical that is mono- or poly-substituted by $OR_4$ and/or $SR_4$, it being possible for the substituents $OR_4$ and $SR_4$ to form 5- or 6-membered rings, via the radicals $R_4$ or with one of the carbon atoms of the heteroaryl ring.

11. A process for the photopolymerization with radiation of wavelengths over 390 nm, wherein as a photosensitive acid donor a compound of the formula Ia

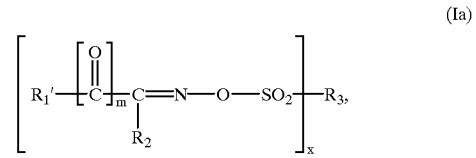

(Ia)

wherein m is 0 or 1 and x is 1 or 2;

$R_1'$ is phenyl mono- or poly-substituted by $OR_4$ and/or $SR_4$, it being possible for the substituents $OR_4$ and $SR_4$ to form 5- or 6-membered rings, via the radicals $R_4$ or with one of the carbon atoms of the phenyl ring, or $R_1'$ is naphthyl, anthracyl or phenanthryl, the radicals naphthyl, anthracyl and phenanthryl being mono- or poly-substituted by $OR_4$ and/or $SR_4$, it being possible for the substituents $OR_4$ and $SR_4$ to form 5- or 6-membered rings, via the radicals $R_4$ or with one of the carbon atoms of the naphthyl, anthracyl or phenanthryl ring, or $R_1'$ is a heteroaryl radical that is substituted by $OR_4$ and/or $SR_4$, it being possible for the substituents $OR_4$ and $SR_4$ to form 5- or 6-membered rings, via the radicals $R_4$ or with one of the carbon atoms of the heteroaryl ring;

$R_2$ is $C_2$–$C_6$alkoxycarbonyl, CN, $C_1$–$C_4$haloalkyl, $S(O)_nC_1$–$C_6$alkyl, or unsubstituted or $C_1$–$C_{12}$alkyl-substituted $S(O)n$-$C_6$–$C_{12}$aryl, wherein n is 1 or 2; or $R_1'$ and $R_2$, if appropriate together with the CO group, form a 5- or 6-membered ring that is substituted by $OR_4$ or $SR_4$ and that may additionally be interrupted by O, S, CO and/or by $NR_5$ and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or mono- or poly-substituted by halogen, $C_1$–$C_4$haloalkyl, CN, $NO_2$, $C_1$–$C_{16}$alkyl, $OR_4$, $COOR_7$, —OCO—$C_1$–$C_4$alkyl, $SO_2OR_7$ and/or by $R_5R_6N$, or $R_3$, when x is 2, is $C_2$–$C_{12}$alkylene, phenylene, naphthylene,

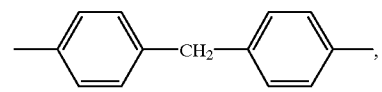

diphenylene or oxydiphenylene, the radicals phenylene, naphthylene,

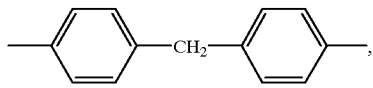

diphenylene and oxydiphenylene being unsubstituted or substituted by $C_1$–$C_{12}$alkyl;

$R_4$ is hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl and that may additionally be interrupted by —O—;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_1$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring that may be interrupted by —O— or by —NR$^4$—; and $R_7$ is $C_1$–$C_{12}$alkyl that is unsubstituted or substituted by OH and/or by $C_1$–$C_4$alkoxy and that may additionally be interrupted by —O—,
  is added to at least one compound that can be crosslinked under the action of an acid and/or at least one compound the solubility of which is altered under the action of an acid, and
  irradiating the resulting composition with radiation of wavelengths over 390 nm.

12. A process according to claim 11, wherein in the compound of formula Ia, $R_1'$ is phenyl substituted by $OR_4$ and/or $SR_4$, it being possible for the substituents $OR_4$ and $SR_4$ to form 5- or 6-membered rings, via the radicals $R_4$, or with one of the carbon atoms of the phenyl ring.

13. A process according to claim 11, wherein in the compound of formula Ia, $R_1'$ is a heteroaryl radical that is substituted by $OR_4$ and/or $SR_4$, it being possible for the substituents $OR_4$ and $SR_4$ to form 5- or 6-membered rings, via the radicals $R_4$ or with one of the carbon atoms of the heteroaryl ring.

14. A process for the photopolymerization with radiation of wavelengths over 390 nm, wherein as a photosensitive acid donor a compound of the formula Ia

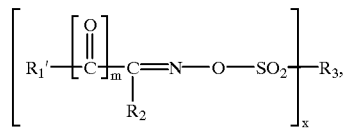

m is 0 or 1 and x is 1 or 2;

$R_1'$ is phenyl substituted by one or more of the radicals $OR_4$ and/or $SR_4$ it being possible for the substituents $OR_4$ and $SR_4$ to form 5- or 6-membered rings, via the radicals $R_4$ or with one of the carbon atoms of the phenyl ring, with the proviso that when the phenyl ring is substituted by methoxy at least one further substituent must be present on the ring, or $R_1'$ is naphthyl, anthracyl or phenanthryl, the radicals naphthyl, anthracyl and phenanthryl being substituted by $OR_4$ and/or $SR_4$, it being possible for the substituents $OR_4$ and $SR_4$ to form 5- or 6-membered rings, via the radicals $R_4$ or with one of the carbon atoms of the naphthyl, anthracyl or phenanthryl ring, or $R_1'$ is a heteroaryl radical that is substituted by $OR_4$ and/or $SR_4$, it being possible for the substituents $OR_4$ and $SR_4$ to form 5- or 6-membered rings, via the radicals or with one of the carbon atoms of the heteroaryl ring;

$R_2$ is $C_2$–$C_6$alkoxycarbonyl, CN, $C_1$–$C_4$haloalkyl, $S(O)_n C_1$–$C_6$alkyl, unsubstituted or $C_1$–$C_{12}$alkyl-substituted $S(O)n$-$C_6$–$C_{12}$aryl, wherein n is 1 or 2; or $R_1'$ and $R_2$, if appropriate together with the CO group, form a 5- or 6-membered ring that is substituted by $OR_4$ or $SR_4$ and that may additionally be interrupted by O, S, $NR_5$ and/or by CO and to which one or more benzo radicals may be fused;

$R_3$, when x is 1, is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or substituted by one or more of the radicals halogen, $C_1$–$C_4$haloalkyl, CN, $NO_2$, $C_1$–$C_l6$alkyl, phenyl, $OR_4$, $COOR_7$, —OCO—$C_1$–$C_4$alkyl, $SO_2OR_7$ and/or by $R_5R_6N$, or $R_3$, when x is 2, is $C_2$–$C_{12}$alkylene, phenylene, naphthylene,

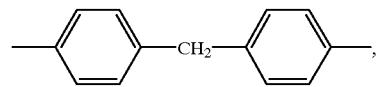

diphenylene or oxydiphenylene, the radicals phenylene, naphthylene,

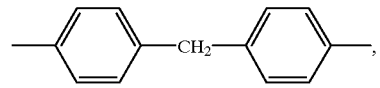

diphenylene and oxydiphenylene being unsubstituted or substituted by $C_1$–$C_{12}$alkyl;

$R_4$ is hydrogen or $C_1$–$C_{12}$alkyl that is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—, or $R_4$ is phenyl;

$R_5$ and $R_6$ are each independently of the other hydrogen or $C_1$–$C_{12}$alkyl that is unsubstituted or substituted by OH, $C_1$–$C_4$alkoxy, $C_1$–$C_{12}$alkylsulfonyl, phenylsulfonyl, (4-methylphenyl)-sulfonyl and/or by $C_1$–$C_6$alkanoyl and that may additionally be interrupted by —O—, or $R_5$ and $R_6$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_5$ and $R_6$, together with the nitrogen atom to which they are bonded, form a 5-, 6- or 7-membered ring that may be interrupted by —O— or by —NR$_4$—; and $R_7$ is $C_1$–$C_{12}$alkyl that is unsubstituted or substituted by OH and/or by $C_1$–$C_4$alkoxy and that may additionally be interrupted by —O—, is added to at least one compound that can be crosslinked under the action of an acid and/or at least one compound the solubility of which is altered under the action of an acid, and irradiating the resulting composition with radiation of wavelengths over 390 nm.

* * * * *